(12) United States Patent
Dean

(10) Patent No.: US 7,166,688 B1
(45) Date of Patent: *Jan. 23, 2007

(54) CHELATION COMPOSITIONS

(75) Inventor: Frank Dean, Houston, TX (US)

(73) Assignee: LidoChem, Inc., Hazlet, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/672,847

(22) Filed: Sep. 25, 2003

Related U.S. Application Data

(62) Division of application No. 09/611,521, filed on Jul. 8, 2000, now Pat. No. 6,870,026.

(51) Int. Cl.
*C06G 63/08* (2006.01)

(52) U.S. Cl. ............... 528/354; 528/363; 71/27

(58) Field of Classification Search ............... 528/354, 528/363; 71/27
See application file for complete search history.

(56) References Cited

U.S. PATENT DOCUMENTS

| | | | |
|---|---|---|---|
| 2,992,223 A | 7/1961 | Frazza et al. | |
| 3,399,990 A | 9/1968 | Humphrey et al. | |
| 3,578,679 A | 5/1971 | Caruso et al. | |
| 3,632,646 A | 1/1972 | Hageman | |
| 3,883,342 A | 5/1975 | Abramitis et al. | |
| 4,590,260 A | 5/1986 | Harada et al. | |
| 4,696,981 A | 9/1987 | Harada et al. | |
| 4,839,461 A | 6/1989 | Boehmke | |
| 5,057,597 A | 10/1991 | Koskan | |
| 5,116,513 A | 5/1992 | Koskan et al. | |
| 5,152,902 A | 10/1992 | Koskan et al. | |
| 5,219,952 A | 6/1993 | Koskan et al. | |
| 5,221,733 A | 6/1993 | Koskan et al. | |
| 5,286,810 A | 2/1994 | Wood | |
| 5,292,859 A | 3/1994 | Ford et al. | |
| 5,296,578 A | 3/1994 | Koskan et al. | |
| 5,363,412 A | 11/1994 | Hartman et al. | |
| 5,372,626 A | 12/1994 | Zivion et al. | |
| 5,468,838 A | 11/1995 | Boehmke et al. | |
| 5,549,729 A | 8/1996 | Yamashita | |
| 5,668,086 A | 9/1997 | Tadayuki et al. | |
| 5,763,634 A | 6/1998 | St. George et al. | |
| 5,797,976 A | 8/1998 | Yamashita | |

FOREIGN PATENT DOCUMENTS

| | | | |
|---|---|---|---|
| CA | 2285308 | * | 10/1998 |
| JP | 08012631 | * | 1/1996 |

* cited by examiner

*Primary Examiner*—Duc Truong
(74) *Attorney, Agent, or Firm*—Karen B. Tripp

(57) ABSTRACT

Biodegradable chelating agents comprising a substituted iminodisuccinic acid having six coordination sites and a simple method for making same are disclosed. The method calls for mixing together an acid anhydride or lactone with a polyfunctional amine to obtain an amide which is further reacted with an amine. The chelating agents are particularly useful for agricultural applications such as fertilizers.

19 Claims, No Drawings

CHELATION COMPOSITIONS

RELATED APPLICATION

This patent application is based in part on U.S. Provisional Patent Application No. 60/154,469, filed Sep. 17, 1999, and this patent application is a division of U.S. patent application Ser. No. 09/611,521, filed Jul. 8, 2000 now U.S. Pat. No. 6,870,026.

BACKGROUND OF THE INVENTION

I. Field of the Invention

This invention relates to chemical compositions having utility as chelating agents and particularly to biodegradable chelating agents. This invention particularly relates to chelating agents having utility in agriculture and particularly in fertilizers.

II. Description of Relevant Art

In agriculture, metal ions are essential nutrients for plant growth, development, and disease resistance. Plant nutrient insufficiencies, because of the unavailability or exhaustion of metal ions, are very often the cause of poor plant growth and development. Crop deficiencies occur at extremely low levels of metal deficiency, that is to say, at levels of parts/million in the plant tissue.

Both soil and foliar application of chelated metal ions may prevent, correct or minimize crop mineral deficiencies. Chelated complexes have been favored because the chelated metal ions remain soluble in different or changing environments. Conventional products have used synthetic chelates. However, even though widely accepted as the best method for the administration of metal ions, synthetic chelates persist in the environment. Therefore, less persistent, yet still efficient, chelating systems have been sought.

The use of naturally occurring organic acids, and their derivatives, as chelating agents to provide an inexpensive and biodegradable alternative has been proposed. However metal chelates of citric acid were reported as unstable at a pH above 7 and as having inferior properties to the synthetic chelating agents.

Because some synthetic chelates are not biodegradable, the uses of such compounds are being regulated in many parts of the world. Often the use of naturally occurring organic acids and organic bases that readily degrade are not always efficacious. The use of a synthetic chelate that biodegrades may substitute for the synthetic compound with environmental persistence and still be effective. The present invention solves those needs.

A variety of methods for preparing polysuccinimide with subsequent hydrolysis to polyaspartic acid (or salts) have been described in the literature and patents. In addition uses of those compounds as chelates have also been reported.

U.S. Pat. No. 4,590,260 to Harada et al. teaches that copoly (amino acids) are produced by heating a mixture of at least one amino acid with at least one of ammonium malate, ammonium maleate or ammonium fumarate, or ammonium salts of malic, maleic or fumaric acid monoamide, or malic, maleic or fumaric acid monoamide or diamide, and hydrolyzing the reaction mixture under neutral or alkaline condition. The method is said to be simple and easy to handle, and therefore, suitable for industrial applications.

U.S. Pat. No. 5,362,412 to Hartman, et al., teaches use of iminodisuccinic as a nonphosphorus-containing biodegradable stabilizer, and U.S. Pat. No. 5,468,838 to Boehmke; teaches a process for the preparation of polysuccinimide, polyaspartic acid and their salts, where, polysuccinimide, polyaspartic acid and their salts are prepared by reaction of maleic anhydride and ammonia, polycondensation of the resulting product in the presence of a solubilizing agent and, if appropriate, hydrolysis.

Patent Application Publication WO9845251A1 of GROTH, et al., entitled "Preparation and Use of Iminodisuccinic Acid Salts," teaches that iminodisuccinic acid alkaline salts can be prepared by reacting maleic acid anhydride (MAA), alkali metal hydroxide NH3 and water in a molar ratio of MAA: alkali metal hydroxide: NH3: H2O=2:0.1–4: 1.1–6.5: 5–30 at 70–170° C. and 1–80 bar for 0.1–100 hours. The reaction mixture is mixed with additional $H_2O$ and optionally alkali metal hydroxide and is freed distillatively of $NH_3$ at 50–170° C. and 0.1–50 bar and then set at a 0.1–50 bar and then set at a solids content of 5–60 weight % using $H_2O$. The iminodisuccinic acid alkaline salts are said to be useful for increasing the brightness and brilliance of plant fibres in paper manufacture.

Patent Application Publication No. JP8012631, of Yamamoto Hiroshi also teaches a procedure for production of iminodisuccinic acid and it's alkali metal salt and a biodegradable chelating agent containing the same. In this procedure, a tetraalkali metal salt of iminodisuccinic acid is obtained by adding a half ester of maleic acid to aspartic acid or ammonia under an alkaline condition followed by hydrolysis and evaporation to dryness. A second objective iminosuccinic acid is obtained by the above addition reaction followed by hydrolysis and then addition of sulfuric acid (without conducting an evaporation to dryness). In these processes, use of L-aspartic acid in place of the ordinary aspartic acid is said to produce D,D-form-free iminodisuccinic acid and a tetraalkali metal salt thereof. Alternatively, L,L-iminodisuccinic acid is said to be selectively obtained by prior crystallization and/or washing of a mixture of the L,L-form and D,D-form of iminodisuccinic acid or a tetraalkali metal salt thereof. The other "objective biodegradable chelating agent" is said to contain, as the active ingredient, the D,D-form-free iminodisuccinic acid and/or an alkali metal salt thereof.

U.S. Pat. No. 4,839,461 to Boehmke describes a procedure for preparation of polyaspartic acid from maleic anhydride, water and ammonia. In the procedure, maleic anhydride is converted into a monoammonium salt in an aqueous medium with addition of concentrated ammonia solution. The water must be evaporated out of the aqueous solution, and the monoammonium salt is subjected to polycondensation to give poly succinic imide in the melt at temperatures of, for example, 125 degrees to 140 degrees Centigrade. Viscous phases which are difficult to control industrially are passed through during this procedure. In the course of the condensation, thermal insulation may occur, which severely delays heat transfer to end the reaction. Suitable apparatuses for detaching the wall layers and thorough mixing are proposed in the specification. For subsequent neutralization for preparation of salts, the mixture must again be converted into the liquid phase. This solution must be evaporated again for preparation of the solid salts A series of patents to Koskan et al., U.S. Pat. No. 5,057,597; U.S. Pat. No. 5,116,513; U.S. Pat. No. 5,152,902 and U.S. Pat. No. 5,221,733, teach methods for thermal polymerization of aspartic acid in a fluidized bed to form polysuccinimide which is then hydrolyzed to polyaspartic acid (sodium salt) using sodium hydroxide. Uses of polyaspartic acid as calcium carbonate, calcium and barium sulfate and calcium phosphate scale inhibitors are also described in these patents.

U.S. Pat. No. 5,219,952 and U.S. Pat. No. 5,296,578 to Koskan & Meah teach production of polysuccinimide and polyaspartic acid (and salts) from maleic anhydride, water and aqueous ammonia. Polysuccinimide is said to be produced in at least 90% of theoretical yield by heating the maleic anhydride, water, ammonia mixture at 220 degrees–260 degrees Centigrade.

U.S. Pat. No. 4,696,981 to Harada & Shimoyama teaches preparation of polysuccinimide from precursors of aspartic acid such as monoammonium, diammonium, monoamide, diamide and monoamideammonium salts of malic, maleic and fumaric acid and mixtures of these materials by irradiating them with microwaves. The resulting polysuccinimide is hydrolyzed to form polyaspartic acid. Similarly mixtures of at least one amino acid and precursors of aspartic acid are taught to be irradiated with microwaves followed by hydrolysis to produce copolyamino acids of aspartic acid.

U.S. Pat. No. 5,286,810 to Wood discloses the preparation of higher molecular weight copolymers of polyaspartic acid said to be suitable for the inhibition of scale deposition by reacting maleic acid and ammonia in stoichiometric excess with a diamine or a triamine at 120 degrees–350 degrees Centigrade. The resulting copolymers of polysuccinimide are said to be converted to a salt of the copolymer of polyaspartic acid by hydrolysis with a hydroxide.

U.S. Pat. No. 5,292,858 to Wood teaches copolymers of polyaspartic acid prepared by making maleic half esters followed by addition of an equivalent of ammonia and an amine and heating to 120 degrees–350 degrees Centigrade. When an equivalent of alcohol is distilled off, a copolymer of polysuccinimide is said to be formed, which is hydrolyzed with hydroxides to form amide copolymers of polyaspartic acid.

U.S. Pat. No. 5,763,634 to St. George, et al. teaches a process for preparing ferric chelate solutions of alkali metal polyamino succinic acids.

Notwithstanding these various known procedures, prior art systems involving succinic acids, when used for chelation have failed to achieve their assumed bonding potential, rendering prior art compounds less attractive as chelating agents in the fertilizer market place. A reference by T. N. Polynova, L. A. Zassourskaya and M. A. Porai-Koshits, entitled, "Crystal Structures of d-Transition Metal Complexes with Iminodisuccinic Acid," published by the Chemical Department, Moscow State University, Moscow, 119899, Russia discusses the problem.

This Poynova et al. reference teaches that "in complexation with d-transition metals, the ligand-iminodisuccinic acid (H4ids) does not realize all its coordination possibilities in any of the complexes studied by X-ray analysis. Potentially, the H4ids ligand is pentadentate, but in compounds [Co(H2O)6][Coids(en)]2. 4H2O (I) and [ZnH2ids(H2O)2] (II) ids4- and H2ids2-ligands are tetradentate regardless of the differences in aprotonization, stoichiometric composition and valent state of complexing atoms. The coordination of Co(III) and Zn(II) in the form of a distorted octahedron is made up of the N-atom and three O— atoms of the H4ids ligand as well as of two N-atoms of the en ligand or two water molecules in I and II respectively. Hence, the three metallocycles are formed as one [[beta]]-carboxyl branch [which] remains uncoordinated by the metal (aprotized in I and protonized in II). In I an intramolecular H-bond is formed between the free [[beta]]-carboxyl and the amino group of ethylene-diamine. In II the intramolecular H-bond is not formed: H-atoms (one of them connected with N, another, with the O-atom of the uncoordinated [[beta]]-carboxyl group) form intermolecular H-bonds".

Thus, the prior art teaches that while the Iminodisuccinates have value, they fail to provide adequate chelation of metal ions, particularly for uses such as in phosphate fertilizer solutions. Such failure stems from several qualities of the compound. The most efficacious of chelation compounds have at least six nonbonded electron pairs; and most mineral ions share a coordination number of six. Because some isomers of Iminodisuccinate are tetradente, the complexes are vulnerable to carbonate, hydroxide, and, phosphate participation in the complex and such complexes are insoluble. Further, iminodisuccinic isomers have the ability to donate four electron pairs, and with the prior art methods of synthesis, there are a number of isomers that can not provide five pairs because of bond strain or bond angle limitations. Iminodisuccinate is mostly found as a tetradente-chelating agent. Being tetra dente prevents the compound from being suitable as a commercial chelating agent for use in agriculture and industry, and particularly for example in phosphorus fertilizers.

Accordingly, there has been a long felt, and unfulfilled need for more efficient, more economical, and more environmentally friendly chelation methods and compositions. These methods and compositions could be used to deliver micronutrient levels of trace metals to plants, to aid in delivery of other horticultural and agricultural chemicals, and, for fertilizers with required metal nutrients necessary for plant growth, development, and disease resistance. The present invention meets such needs.

SUMMARY OF THE INVENTION

Chelating compositions comprising modified iminodisuccinic acid and a simple method of making such acid are disclosed. The modified iminodisuccinic acids of the invention have one or more of the following six formulas:

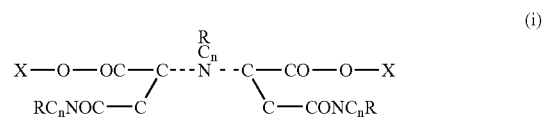

(i)

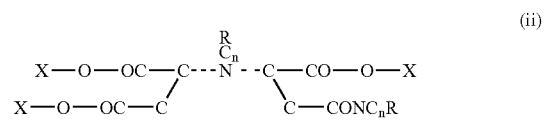

(ii)

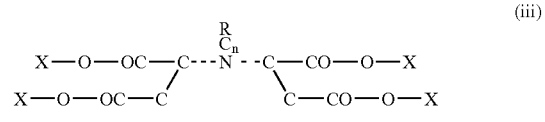

(iii)

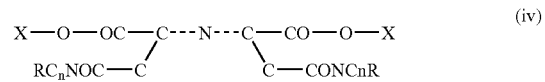

(iv)

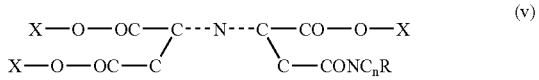

(v)

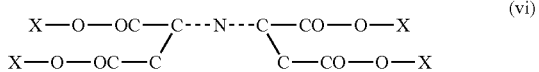

(vi)

Where X may be H, alkali, alkaline earth, ammonium-substituted radical, ammonium or transition metal;

Where n may be 1 to 10; and

Where R may be a Lewis base capable of donating a nonbonded pair of electrons.

In preparing the modified iminodisuccinic acids of this invention, an acid anhydride or lactone is mixed with a first polyfunctional amine and allowed to react to form an amide. A second polyfunctional amine is then added to the amide in the water to form an iminodisuccinic acid.

These chelating compositions are useful when biodegradable compositions are desired, such as in fertilizers, for example.

DETAILED DESCRIPTION OF THE PREFERRED EMBODIMENT

Introduction:

Most metal ions react with electron pair donors to form chemical complexes. These donors (ligands) must have at least one pair of unshared electrons. A chelate is a cyclic complex that is formed when two or more donor groups contained in a single ligand bond a cation. Polydentate ligands (many tooth ligands) are preferred because the lower entropy of these systems is thought to prevent dissociation of the complex during normal equilibrium shifts in aqueous systems.

The efficacy of a chelate is described by the stability constants ($K_f$) of the chelation systems. A stability constant is a complex formation proportionality constant; that is, the chelation reaction is dependent upon a given concentration of both the metal ion and ligand in solution. The higher the stability constant, the lower the concentrations of complexing agent and cation necessary for the chelation reaction to occur (or remain stable).

Carboxylic acids are known to complex metal ions only subsequent to $H^+$ or acid dissociation, that is, the organic acid-metal ion complexes are pH dependent. The highest cation stability constants are found in solutions with a pH greater then 7—for EDTA the greatest stability is approached at a pH greater then 12. The endpoint of an organic acid titration is the lowest pH value needed for the greatest abduction, that is, the endpoint is the lowest pH necessary for the optimum (highest) cation stability constant.

These systems are often illustrated with the equation:

$$\frac{K_1 * K_2 * K_3 * K_4}{[H^+]^4 + K_1[H^+]^3 + K_1 * K_2[H^+]^2 + K_1 * K_2 * K_3[H^+]^1 + K_1 * K_2 * K_3 * K_4} = \alpha^4$$

Where $\alpha$ is a stability constant coefficient for the determination of the systems actual stability constant; and, the $K_n$ values are the $K_a$ dissociation constants of the functional groups involved in the creation of a complex. With this, one can use the $K_b$ of the organic base to determine the compounds $K_a$.

$$1.0*10^{-4} = K_a$$

$K_b$

With these equations one can readily determine the actual stability constants, alpha values, and the relative concentration of each complexed species in a solution at a given pH.

The present invention relates to methods for the chelation of metal ions from their oxides and salts. The reaction products of these methods are useful for agricultural, industrial, and environmental purposes.

The present invention provides methods, syntheses, and improved compositions for chelation; also, for the methods, synthesis, compositions, and uses of fertilizer compositions for delivering trace levels of metal ions to soils and plant tissues. The compositions and methods of the present invention provide chelated metal ions as a fertilizer additive.

Compositions of Matter and Method of Making Same:

The present invention provides new methods of adding coordination sites to the iminodisuccinic, with the appropriate bond angles and the ability to coordinate six sites. The present invention thus relieves the high cost associated with prior synthetic chelates, improves the synthesis methods through simplification, and adds functionality and utility, therefore, rendering the end compositions suitable for broad commercial use.

The simplicity of synthesis and usefulness of these present compounds will become apparent when compared to prior methods. The greatest burden to overcome for the iminodisuccinate compound synthesis is the ability to resolve the isomerization and utilize all of it's bonding potential. The DL isomer can not coordinate fully because of bond angle limitations, thus, iminodisuccinic usefulness is limited to few economic pursuits. For commercial viability a chelating agent has to have broad application appeal and efficacy. Without the ability to coordinate the number of sites for a given cation's coordination number the chelating compound will not be successful in the marketplace.

The preferred synthesis route would reduce the amount of equipment necessary for high yielding, low cost acid amide chelating agents suitable for commercial applications. For instance, U.S. Pat. No. 4,590,260 to Harada et al., teaches copoly (amino acids) are produced by heating a mixture of at least one amino acid with at least one of ammonium malate, ammonium maleate or ammonium karate, or ammonium salts of malic, maleic or fumaric acid monoamide, or malic, maleic or fumaric acid monoamide or diamide, and hydrolyzing the reaction mixture under neutral or alkaline condition.

The methods of the present invention do not need heat applied for condensation, nor do the methods require hydrolysis of a polymer. The compounds are water borne, eliminating the need for hydrolysis. Thus, the methods of the present invention provide for a simplified synthesis with fewer raw materials and hence lower production cost.

The preferred process or method of the present invention may be described as follows:

Acid anhydride (or lactone)+polyfunctional amine->N-polyfunctional acid common name amide Then, N-polyfunctional acid common name amide+polyfunctional amine->imido di N-polyfunctional acid common name amide Or, Acid anhydride (or lactone)+polyfunctional amine->N-acid common name polyfunctional amide Then, N-acid common name polyfunctional amide+acid anhydride+alkali metal hydroxide+R—NH$_2$->amino acid alkali metal salt N-common name polyfunctional amide Where R is a hydrogen or organic radical.

Either method of synthesis of this invention has the ability to produce a chelating compound with at least six coordinating nonbonded electrons; and at least five of the nonbonded electron pairs may participate in coordination without steric hindrance or bond angle limitations.

For instance or example:

Maleic anhydride+ethanol amine->N-ethanolmaleicamide

Then, in the same vessel in an aqueous phase,

2 N-ethanolmaleicamide+NH$_3$->isomers of N,N-amino diethanolsuccinicamide

In the first step, the primary or secondary amide reaction will occur to yield essentially 100% of the desired product. Then the heat from the amide reaction fuels the radical reaction, in the same vessel at the same time, alkali metal hydroxide, NH3, or polyfunctional amine and water further react producing poly functional amine substituted amino disuccinic acid or salt. All processes occur without the heating commonly needed in prior art methods for condensing, and occur with fewer raw materials and less equipment than prior art methods, thereby offering an economic advantage over those methods.

I have discovered that all isomers with the added Lewis base functionality (or with Lewis base functional groups) from either the acid amide or the additional groups attached to the imido group, have the ability to donate at least five nonbonded pairs without hindrance or bond strain; unlike the non-substituted Iminodisuccinates' isomers, the compounds of the present invention may find broad commercial use.

Another unique feature of the compounds of the present invention is that they are water borne and hydrolysis of a polymer will not be necessary. Therefore, with one reaction vessel, at ambient pressure, without the need for heating, the N,N-amino disuccinic amides of the present invention can be prepared.

Without intending to limit the invention, it is presently believed that the effectiveness of the compositions of the present invention for chelation is achieved by adding the amide functionality to a carboxyl group, or by an organic substitution with an additional Lewis base functionality to the imino group, such that either the bond angles are changed or there are additional Lewis bases capable of donating non bonded pairs of electrons, thereby allowing any and all of the isomers to participate in the chelation and coordinate with six sites. A chelation compound suitable for phosphorus fertilizer compositions is thus produced according to the present invention.

The synthesis of the present invention can also be adapted to blend N-ethanolmaleicamide with a salt of malic acid to produce the isomer mixtures of iminodi—N-ethanolsuccinicamide, and aspartic—N-ethanolsuccinicamide, and their salts. Once the amide functionality is added to a carboxyl group, or, by an organic substitution with additional Lewis base functionality to the imino group, the compounds become useful as chelating agents, in that, either addition allows for one molecule to coordinate up to six sites of an ion without bond angle limitations for a commercially viable synthetic chelating agent that can coordinate as well as the non-biodegrading synthetic chelating agents presently in commerce.

The more preferred organic amines for use in this invention are the difunctional amines selected from the group consisting of organic diamines, hydroxylamines, polyamines, poly hydroxylamines, acid amines, and mixtures thereof. In contrast to the teachings of U.S. Pat. No. 5,763,634 to St. George, in the present invention, the amide is reacted with the anhydride or lactone to form an acid amide or amine prior to the reaction with the maleic moiety double bond. A polyamine radical does not attach to the double bond position of the maleic acid moieties, and, therefore, a "poly amino poly succinic" is not produced, unlike the teachings of U.S. Pat. No. 5,763,634 to St. George. The amine substitution on the carboxyl carbon according to the present invention, as opposed to the substitution on the second or third carbon in prior art methods, results in the newly formed substituted Iminodisuccinates of the present invention, which do not have the limitations reported in the prior art and which are therefore suitable for phosphorous fertilizer compositions, fertilizer additives, and industrial needs.

Uses:

Broadly, the metal ions in a fertilizer additive may be the biologically required trace metals. The metal ions in an additive solution of the present invention are typically selected from the group consisting of the alkaline earth and transition metals. Preferred compositions include at least one metal selected from the group consisting of calcium, magnesium, manganese, iron, cobalt, copper, zinc, molybdenum, and mixtures thereof.

In the present invention, the fertilizer additive solutions may be blended with conventional, liquid fertilizers to produce clear, liquid fertilizer compositions. The liquid fertilizers are preferably chosen from the group of fertilizers containing at least one nutrient selected from the group consisting of nitrogen, phosphorus and potassium. Such liquid fertilizers are commonly referred to as N—P—K fertilizers.

In another aspect of this invention, Iminodisuccinates may be used as non-ortho phosphate containing fertilizer additives. Although some complexes of Iminodisuccinates have been disclosed, there is no description in the prior art of how to make concentrated solutions of these complexes for fertilizer compositions.

On occasion, the "fertilizer additive" of this invention may be applied to the plant or soil independently or alone, without admixture with N—P—K fertilizers or other compounds. Also, chelated metal cations may be delivered at some quantity or concentration to inhibit or prevent disease. Still other uses or applications may apply the chelated materials by admixing to other materials. The chelating compounds may be added to the plant, soil, or seed.

Fertilizer additives and compositions in accord with the present invention may be prepared by the following method. An acidic solution is prepared by adding one of the modified Iminodisuccinates to water. A metal salt, preferably the soluble salts, selected from the salts of biologically required trace metals, preferably the alkaline earth and transition metals, is dissolved in the acidic solution. The acidic solution containing metal ions is then buffered by adding a sufficient quantity of an inorganic lewis base or inorganic or organic amines or combinations. The resulting solution of complexed metal ions is preferably and typically clear and free of any precipitate. These solutions have been found to be quite stable and to provide excellent liquid fertilizer additives useful to provide trace metals to plant tissue, soils and seed.

In another method of this invention the additives and compositions in accord with the present invention may be prepared by the following method. A neutral or basic solution is prepared by adding the salts of the present invention to water and later adding the alkaline earth or transition metal salts to the blend. The resulting solution of complexed metal ions is typically clear and free of any precipitate. These solutions have been found to be quite stable and to provide excellent liquid fertilizer additives useful to provide trace metals to plant tissue, soils, and seed. The pH may be adjusted by adding a base or an acid.

Many of the chemicals used in agricultural and industrial practices currently use surfactants. Poly functional amide substituted iminodisuccinic acid or salt may act as emulsification agents, therefore, the use of inorganic Lewis bases or inorganic and organic amines or combinations of salts of poly functional amide substituted iminodisuccinic acid or salt could eliminate the need for the admixture surfactants. Industrial applications for this system of chelation include metal finishing, metal cleaning, steel processing, paint stripping, electroplating, aluminum processing, dish washing, glass processing, and any process that has the need to complex the unwanted cation concentration in solution, or, remove rust, scale, smut and coatings from valued surfaces. The concentration of these compounds is dependent on the systems needs.

For metal finishing, metal cleaning and steel processing, the compounds of the invention can be used to sequester hard water ions that may complex with alkaline cleaners and form precipitates. The deposition of these insolubles may be undesirable on equipment or the surface to be cleaned. The concentration of the polyfunctional amine substituted Iminodisuccinates of this invention are dependent on the systems needs. Because alkaline baths are used to remove rust, scale, smut and coatings from valued surfaces, the present compounds are well suited for these processes.

For paint stripping formulations the addition of the compounds of the present invention may help in sequestering the pigments of the coatings being removed. This sequestering ability may help minimize the number of stripping applications by preventing the pigments from adhering to the surface being cleaned. Because alkaline baths are used in stripping processes the present compounds are well suited for these processes. The concentration of these organic compounds is dependent on the systems needs.

Because electroplating requires the deterioration of an anode and undesirable impurities may interfere with the wanted reactions, the compounds of the present invention are well suited for these processes. These compounds can sequester undesirable impurities; therefor, increasing the plating bath efficacy.

Hydrated aluminum oxide will cause damage to the heating coils and etch tanks in the aluminum etching industry. The compounds of the present invention can sequester undesirable impurities; therefor, increasing the etching bath efficacy. The concentration of these organic compounds is dependent on the systems needs.

The equipment used for the processing and cleaning of glass, ceramics, and plastics can accumulate unwanted metal salts and carbonates. The use of the present compounds can sequester iron and hard water contaminants that cause that buildup. The chelated ions prevent that build up. The concentration of these organic compounds is dependent on the systems needs.

Another useful aspect of this invention is directed to novel fertilizer additives and compositions useful for delivering trace levels of metal ions to plant tissue in chelated forms. These additives and compositions are prepared using a novel combination of chelating agents to complex the metal ions and to control the pH of the additive solution. Some applications may include the use of poly functional amide substituted iminodisuccinic acid or salt to deliver pH sensitive biologically active chemicals, and, those chemicals may include herbicides or pesticides, and the buffering capacity and/or the complexing ability of the compounds may prove to minimize or add to the efficacy of those compounds.

The soluble salts, hydroxides, and oxides are the preferred source of metals. While not limiting the scope of the present invention in as much as the present method will also chelate the metal ions of chloride, sulfate, nitrate, hydroxide and carbonate and other biologically compatible salts of the cations, these salts are more expensive per unit of metal cation, commonly less pure, and some have been associated with ecological damage. It is believed some salts may interfere with the efficacy of some biologically active compounds.

Metal oxides and hydroxides are preferred because they are significantly less expensive per unit of metal cation, are usually more pure, and are less toxic to the environment than their inorganic anion counterparts. The metal ions are chelated using the present compounds. In the preferred compositions of the present invention metal cations are complexed using poly functional amide substituted iminodisuccinic acid or salt. The difunctional amine offers several advantages over the existing technologies, that is to say, odorless formulations, the capability of the formulator to regulate the buffering of a solution's pH, and increased environmental safety. The difunctional amine, not only neutralizes the excess acid in solution, but may also participate in the formation of the chelated complex via hydrogen bonding and coordinate covalent bonding to create a more stable complex.

For agriculture, a general aspect of the present invention is to provide a formulation for a clear liquid fertilizer additive, comprising water, the present compounds, at least one metal salt wherein the metal is preferably selected from the group consisting of the alkaline earth and transition metals, and inorganic Lewis bases or inorganic or organic amines or combinations. The inorganic lewis bases or inorganic or organic amines or combinations are more preferably selected from the group of polyfunctional amines consisting of organic alkylamines, allylamines, arylamines, diamines, hydroxylamines, polyamines, polyhydroxyamines, acid amines, and mixtures or derivatives thereof.

In the most preferred embodiments, the present invention provides compositions and methods for chelating metal ions from their metal salts wherein the metal is selected from the group consisting of calcium, magnesium, iron, cobalt, copper, zinc, manganese, molybdenum and mixtures thereof, using the present compounds. Such fertilizer additive solutions may be generally referred to hereinafter at times as "fertilizer additives" or "additive solutions". These additive solutions, when used alone or in combination with other compounds, could be used for nutritional purposes, or, as a means to inhibit or prevent the damage caused by pathogens.

It is another aspect of the present invention to provide a clear liquid fertilizer composition comprised of the foregoing fertilizer additive solutions blended with a liquid fertilizer. Any conventional liquid fertilizer may be used.

Typically liquid fertilizers include, for example, the N—P—K fertilizers selected from the group containing at least one nutrient selected from the group consisting of nitrogen, phosphorus and potassium. However, metal ions form insoluble phosphate complexes and synthetic chelates have been known to minimize or prevent the precipitation of those complexes. Although, it is known that prior synthetic chelation methods and compounds help in the delivery of necessary nutrients; it has been reported that foliar application of the synthetic chelation compounds induces secondary nutrient deficiencies. The deficiency occurs after the intended mineral ion is delivered and the synthetic chelate reacts with calcium or magnesium, in and between cells, often times removing the calcium from the cell wall or magnesium from the chlorophyll molecule of a plant. This chelation of calcium and magnesium are induced deficiencies that have prevented application of some chelating compounds to foliage. This induced nutritional deficiency is attributed to the high formation constants of the synthetic chelates. Surprisingly, the formation constants of the compounds of the present invention are four to five orders of magnitude lower than prior art chelates previously used. This reduced formation constant allows the present compounds to be applied to foliage of plants that have previously been neglected or had mineral nutrition delivered by alternative methods.

Another aspect of this innovation is providing an environmentally degradable chelation method to industry. Because synthetic chelating agents are not biodegradable, and use of synthetic chelates are beginning to interfere with life cycles of organisms around the world, this innovation will fill an immediate need.

In still another aspect of the current invention is the growth promoting/regulating ability of these compounds on seedlings. When seed are germinated in solutions containing the described compounds they often show changes in seedling physiology. Branching roots and delayed shoot formation are typical responses.

The fertilizer compositions described above and/or prepared in accord with the foregoing procedures may be applied to the ground surrounding a plant or to the foliage of the plant by conventional methods to deliver readily absorbable trace metals to the plant tissue. Thus, the fertilizer additives and compositions of the present invention are an economical and environmentally friendly source of trace metals for use in a wide range of agricultural applications. The forgoing description of the present invention is susceptible of a broad utility and application. It is therefore readily understood by those persons skilled in the art that many embodiments and adaptations of the present invention other that those herein described will be apparent from or reasonably suggested by the present invention and the foregoing description thereof, without departing from the substance or scope of the present invention. With the foregoing description of the present invention, it is believed that any person reasonably skilled in the art will be able to prepare and utilize the chelated metal ion compositions, the organic compositions, or their mixed salt derivatives described herein. For purposes of illustration, but without limiting the scope and substance of the present invention, the following examples describe several specific embodiments of the compositions prepared in accord with this invention.

EXAMPLE 1

An experimental trial was completed testing the efficacy of the Iminodisuccinates (IDS) of this invention on five different crops. Below is the protocol and tissue analysis for both soil and foliar applied iminodisuccinate chelated mineral salts.

| | Soil treated pots: | | | |
|---|---|---|---|---|
| Crop | A | B (10-34-0) | C 10-34-0 blended with zinc chelated | D 10-34-0 blended with zinc, copper, manganese, and iron chelated |
| 1 Corn | Control | Treated | Treated | Treated |
| 2 Wheat | Control | Treated | Treated | Treated |
| 3 Clover | Control | Treated | Treated | Treated |
| 4 Soybean | Control | Treated | Treated | Treated |
| 5 Alfalfa | Control | Treated | Treated | Treated |

A). The control pots were watered without any further treatments.

B). An ammonium polyphosphate stock solution was prepared by adding 50 ml of the 10-34-0 to 4000 ml of water. Treated plants received 100 ml of the stock solution.

(C). The Zinc stock solution was prepared by blending 10 ml of IDS chelated 9% Zinc to a blend of 50 ml of 10-34-0 with 4000 ml of water. Treated plants received 100 ml of the zinc stock solution.

(D). The mixture of IDS chelated micronutrients was prepared by adding 4 ml of 9% Zinc, 1 ml of 5% Copper, 1 ml of 5% manganese, and 1 ml of 5% Iron. This mixture was then blended with 4000 ml of water and 50 ml of 10-34-0.

| | | Foliar Treated Pots: | | | | | |
|---|---|---|---|---|---|---|---|
| | Crop | 1 Zinc | 2 Copper | 3 Manganese | 4 Iron | 5 Mixture | 6 Control |
| A | Soybean | Treated | Treated | Treated | Treated | Treated | Control |
| B | Corn | Treated | Treated | Treated | Treated | Treated | Control |
| C | Wheat | Treated | Treated | Treated | Treated | Treated | Control |
| D | Alfalfa | Treated | Treated | Treated | Treated | Treated | Control |
| E | Clover | Treated | Treated | Treated | Treated | Treated | Control |

A stock solution for foliar application was prepared by blending 6000 ml of water with T-DAT 09, (Harcross Chemical Company, USA) a surfactant, added to spray mix at 2 drops per liter.

1). 5 ml of 9% zinc was added to 1 liter of stock solution.
2). 5 ml of 5% copper was added to 1 liter of stock solution.
3). 5 ml of 5% manganese was added to 1 liter of stock solution.
4). 5 ml of 5% Iron was added to 1 liter of stock solution.

5). 4 ml of 9% zinc, 1 ml of 5% copper, 1 ml of 5% manganese, and 1 ml of 5% iron was added to 1 liter of stock solution.

6). Stock solution without further addition.

All plants were sprayed until wet. Harvested material was placed in an oven for one day and sent to the lab for tissue analysis. Harvesting occurred thirty days after planting and some plants had not grown enough to get complete lab results reported. The harvested corn plants were cut at the whirl to insure only new leaves would be tested. The soybeans were clipped above the cotyledon. The alfalfa and clover were removed from the soil and the roots were removed. The wheat was cut at the tillering node.

| FOLIAR RESULTS in parts per million | | | | |
|---|---|---|---|---|
| CORN | | | | |
| MICRO | CONTROL | TREATED | CHANGE | % change |
| COPPER | 5.2 | 300 | 294.8 | 5669% |
| IRON | 36.9 | 494 | 457.1 | 1239% |
| MANGANESE | 99.1 | 310 | 210.9 | 213% |
| ZINC | 15.6 | 792 | 776.4 | 4977% |
| MIX | | | | |
| zinc | 15.6 | 1135 | 1119.4 | 7176% |
| copper | 5.2 | 382 | 376.8 | 7246% |
| manganese | 99.1 | 315 | 215.9 | 218% |
| iron | 36.9 | 494 | 457.1 | 1239% |
| WHEAT | | | | |
| MICRO | CONTROL | TREATED | CHANGE | % change |
| COPPER | 10.8 | 157 | 146.2 | 1454% |
| IRON | 94.5 | 334 | 239.5 | 353% |
| MANGANESE | 72.1 | 379 | 306.9 | 526% |
| ZINC | 44.3 | 563 | 518.7 | 1271% |
| MIX | | | | |
| zinc | 44.3 | 729 | 684.7 | 1646% |
| copper | 10.8 | 230 | 219.2 | 2130% |
| manganese | 72.1 | 176 | 103.9 | 244% |
| iron | 94.5 | 323 | 228.5 | 342% |
| CLOVER | | | | |
| MICRO | CONTROL | TREATED | CHANGE | % change |
| COPPER | 9.64 | 227 | 217.36 | 2355% |
| IRON | 130 | 731 | 601 | 562% |
| MANGANESE | 168 | 510 | 342 | 304% |
| ZINC | 56.7 | 1264 | 1207.3 | 2229% |
| MIX | | | | |
| zinc | 56.7 | 1609 | 1552.3 | 2838% |
| copper | 9.64 | 636 | 626.36 | 6598% |
| manganese | 168 | 389 | 221 | 232% |
| iron | 130 | 576 | 446 | 443% |
| SOYBEANS | | | | |
| MICRO | CONTROL | TREATED | CHANGE | % change |
| COPPER | 4.74 | 937 | 932.26 | 19768% |
| IRON | 111 | 557 | 446 | 402% |
| MANGANESE | 230 | 544 | 314 | 137% |
| ZINC | 63.8 | 1000 | 936.2 | 1467% |
| MIX | | | | |
| zinc | 63.8 | 1297 | 1233.2 | 1933% |
| copper | 4.74 | 482 | 477.26 | 10069% |
| manganese | 230 | 375 | 145 | 63% |
| iron | 111 | 376 | 265 | 239% |

| SOIL RESULTS | | | | |
|---|---|---|---|---|
| CLOVER | | | | |
| MICRO | CONTROL | TREATED | CHANGE | % change |
| COPPER | 8.91 | 20.2 | 11.29 | 127% |
| IRON | 143 | 224 | 81 | 57% |
| MANGANESE | 154 | 98.4 | (55.60) | −64% |
| ZINC | 53.4 | 231 | 177.6 | 333% |
| WHEAT | | | | |
| MICRO | CONTROL | TREATED | CHANGE | % change |
| COPPER | 6.79 | 12.1 | 5.31 | 78% |
| IRON | 79.3 | 90.9 | 11.6 | 15% |
| MANGANESE | 71.8 | 76.2 | 4.4 | 6% |
| ZINC | 39 | 93.1 | 54.1 | 139% |
| CORN | | | | |
| MICRO | CONTROL | TREATED | CHANGE | % |
| COPPER | 5.43 | 11.7 | 6.27 | 115% |
| IRON | 45.4 | 82.2 | 36.8 | 81% |
| MANGANESE | 128 | 80.1 | (47.90) | −63% |
| ZINC | 24 | 69.6 | 45.6 | 190% |
| SOYBEANS | | | | |
| MICRO | CONTROL | TREATED | CHANGE | % |
| ZINC | 19.4 | 136 | 116.6 | 601% |

The results above show the efficacy of the iminodisuccinate compounds for providing necessary mineral nutrition to growing plants and seedlings.

EXAMPLE 2

In a preliminary lab synthesis trial 120 grams of monoethanolamine was added to an Erlenmeyer flask submerged in an ice water bath. Then, 28 grams of potassium hydroxide flake was added. Later 49 grams of maleic anhydride was added to the flask with mechanical stirring. The reaction occurred producing an ethanolmaleic amide. The mix was viscous and yellow in color. Upon cooling 49 grams of maleic anhydride was added. Another 28 grams of potassium hydroxide flake was added and 40 ml of water was then blended in. The blend was then allowed to deliquesce over night producing a clear yellow liquid. Compounds were produced having the following formula:

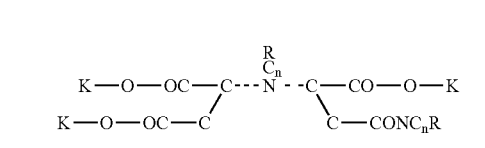

EXAMPLE 3

A 5% manganese II chelate was produced by the following method. In 52.4 grams of water, 16.6 grams of manganese chloride was blended and dissolved. Once the manganese chloride was in solution, 31 grams iminodisuccinic acid, the tetra sodium salt, was blended into the mixture. The solution was pink-brown in color, clear, and suitable for blending with non-ortho phosphate fertilizers for soil, seed, and foliar applications.

EXAMPLE 4

A 5% copper II concentrated chelate solution was prepared from the following method. 138 grams of copper chloride dihydrate was added to 591 grams of water. Once the copper was dissolved and in solution, 270 grams of iminodisuccinate was added to the blend. The solution was dark blue, viscous, and suitable for blending with fertilizers for soil, seed and plant applications.

EXAMPLE 5

A 3% Magnesium solution was prepared from the following method. In 274 grams of water, 306 grams of magnesium sulfate was added. After the solution was clear, 420 grams of iminodisuccinate was added to the blend. The solution was yellow, viscous, and suitable for blending with non-orthophosphate fertilizers for soil, seed, and plant application. This blend may not have long shelf life, however, it would be an acceptable fertilizer additive if produced and used in a short period of time.

EXAMPLE 6

A 7% zinc chelated solution was prepared from the following method. In 440 grams of water, 200 grams of a 30% Zn solution was blended. Once the blend was homogenous, 360 grams of iminodisuccinate tetra sodium salt was blended in. The blend was clear, yellow and suitable for blending with non-orthophosphate fertilizers for soil, seed, and plant applications.

EXAMPLE 7

A 5% manganese solution was prepared form the following formulation. In 34 grams of water, 15.3 grams of manganese sulfate was dissolved. Once the manganese was in solution, 26 grams of EDTA and 3 grams of iminodisuccinate were added. The mixture produced a white paste, which upon the addition of either 21.5 grams of monoethanolamine or potassium hydroxide, dissolved. The solution was clear, pink-brown, and suitable for blending with all fertilizers for soil, plant and seed applications.

EXAMPLE 8

A 5% iron chelate was produced from the following method. In 17 grams of water, 25 grams of ferrous sulfate was blended. Then, 23 grams of EDTA and 15 grams of a 36% iminodisuccinate solution were added. Once such mixture is blended, or 20 grams of potassium hydroxide may be added. The blend was clear, dark green, and suitable for blending with all fertilizers for applications to the seed, soil and plant.

EXAMPLE 9

A 5% copper II concentrated chelate solution was prepared from the following method: 138 grams of copper chloride dihydrate was added to 555 grams of water. Once the copper was dissolved and in solution, 128 grams of iminodisuccinate and 128 grams of EDTA were added to the blend. Additionally 50 grams of potassium hydroxide was blended into the mixture. The solution was dark blue, clear, and suitable for blending with all non-orthophosphate fertilizer solutions for applications to the soil, seed, and plant.

EXAMPLE 10

SYNTHESIS of 2-ethanolaminesuccinic-N-ethanolsuccinicamide. 2 maleic anhydride(s)+3 KOH (aq)+2 monoethanolamine (1)→aspartic-N-ethanolsuccinicamide. (tri potassium salt)

| Compound | Grams per mole | Grams needed for 1 mole |
| --- | --- | --- |
| MALEIC ANHYDRIDE | 98.06 | 196.12 |
| MONOETHANOLAMINE | 61. | 122 |
| POTASSIUM HYDROXIDE | 56 | 168 |
| WATER | 18 | 36 |

Potassium hydroxide was weighed out and added to beaker. The monoethanolamine was then added to the blend and stirred in. Then 98 grams maleic anhydride was added slowly and allowed to react to form the ethanolmaleicamide. 30 grams of ice was added to the beaker and stirred in. Another 98 grams of maleic anhydride was then added to the beaker and reacted to form the tri potassium salt of 2-ethanolaminesuccinic—N-ethanolsuccinicamide. The finished product was light orange red viscous liquid.

EXAMPLE 11

A five percent chelated copper solution was prepared by blending 19 grams of basic copper sulfate in 100 ml of water. Concentrated HCl was added to solubilize the copper. Once in solution, 71 grams of the compound produced in Example 10 was added. The finished solution was dark blue, had a pH of 5, and was free of precipitates. This chelated copper solution is suitable for blending with phosphorus fertilizers.

EXAMPLE 12

Compound Preparation:

A 34% tetrasodium iminodisuccinate solution was protonated with concentrated HCl and crystalized under refrigeration in a dilute water/ethanol. The crystals were then filtered out of the solution and the residual sodium chloride was rinsed from the crystals with ice water. The IDS crystals were then dried.

EXPERIMENTAL

Two sets of 10 corn seed, NCE Hybrid 5817, were then placed on germination trays. One tray had $1/10^{th}$ of a gram of the IDS acid placed in the center of the tray. The seeds were then imbibed with water.

The seeds germinated as expected on day 2. On day 5 the root hairs began to show on the seedlings treated with the IDS. Photos were taken. This procedure was repeated on three occasions with simular results. There were also root hairs on the control set, however, the root hairs were only on short segments of the roots. In the treated set the root hairs appear along the entire length of radical and lateral roots. This would be a substantial increase in the root surface area.

EXAMPLE 13

Protocol for IDS Versus EDTA Chelates Applied to the Soil of Pepper Plants

An experimental trial was completed to test for the efficacy of the Iminodisuccinates (IDS) chelates of the present invention verses the efficacy of EDTA for pepper plants. Below is the protocol and tissue analysis for the soil-applied iminodisuccinate and EDTA chelated mineral salts.

Treatments:

Control—no fertilizer 15-30-15 (fertilizer) alone 15-30-15 plus Cu IDS 15-30-50 plus Cu EDTA 15-30-15 plus Mn IDS 15-30-15 plus Mn EDTA 15-30-15 plus Zn IDS 15-30-15 plus Zn EDTA The standard fertilizer contained no micronutrients. Fertilizer was Hyponex 15-30-15. Each treatment was replicated 3 times. Soil treatments were applied as 50 ml per of the dilute blend of this invention. The pepper plants were transplanted into 1-gallon containers and grown until a suitable size. Plants were treated with the soil-applied chelate. Tissue samples were taken 30 days after the soil treatment had been applied. The peppers were fertilized a month before tissue samples were taken and again nine after the first fertilizer application (or about three weeks before the tissue samples were taken) with 12 grams per gallon of the 15-30-15. One gallon of fertilizer was poured over three replications of each set in the trial. Soil treated pots:

| MICRO | CONTROL | CONTROL ADJUSTED | TREATED | TREATED ADJUSTED | CHANGE IN | % CHANGE |
|---|---|---|---|---|---|---|
| IDS | 8.0 | 4.8 | 38.08 | 10.8 | 6.4 | 68.79 | 30.72 | 81% |
| EDTA | 8.0 | 4.8 | 38.08 | 12.9 | 6.2 | 80.03 | 41.95 | 110% |
| IDS Mn | 117.5 | 4.8 | 559.3 | 105.1 | 6.8 | 719.81 | 160.51 | 29% |
| EDTA Mn | 117.5 | 4.8 | 559.3 | 142.3 | 6.1 | 871.08 | 311.78 | 56% |
| IDS ZINC | 126.0 | 4.8 | 599.76 | 157.7 | 6.4 | 1002.76 | 403.00 | 67% |
| EDTA ZINC | 126.0 | 4.8 | 599.76 | 169.7 | 5.7 | 959.74 | 359.99 | 60% |

| MICRO | CONTROL DRY | TREATED DRY | CHANGE IN WEIGHT | % CHANGE |
|---|---|---|---|---|
| IDS COPPER | 4.8 | 6.4 | 1.63 | 34% |
| EDTA COPPER | 4.8 | 6.2 | 1.46 | 31% |
| IDS | 4.8 | 6.8 | 2.09 | 44% |
| EDTA | 4.8 | 6.1 | 1.36 | 29% |
| IDS ZINC | 4.8 | 6.4 | 1.60 | 34% |
| EDTA ZINC | 4.8 | 5.7 | 0.90 | 19% |

The results above shows the efficacy of the iminodisuccinate compounds for providing necessary mineral nutrition to growing plants and seedlings. The trial shows the iminodisuccinate did as well as the EDTA for availability of the minerals.

EXAMPLE 14

Protocol for IDS Versus EDTA Chelates Applied to Tomato Foliage

An experimental trial was completed to test for the efficacy of the Iminodisuccinates (IDS) chelates of the present invention verses the efficacy of EDTA for tomato plants. Below is the protocol and tissue analysis for the foliar applied iminodisuccinate (IDS) and EDTA chelated mineral salts.

Treatments:

Control—no fertilizer 15-30-15 (fertilizer) alone 15-30-15 plus Cu IDS 15-30-50 plus Cu EDTA 15-30-15 plus Mn IDS 15-30-15 plus Mn EDTA 15-30-15 plus Zn IDS 15-30-15 plus Zn EDTA The standard fertilizer contained no micronutrients. Fertilizer was 15-30-15 Each treatment was replicated 3 times. Foliar treatments were applied as 5 ml per or the IDS chelates of this invention liter of water and then 50 ml of this solution were sprayed over the plants with a hand held sprayer. Tomato plants were transplanted into 1-gallon containers and grown until a suitable size. Plants were treated with the foliar applied chelate. Tissue samples were taken 14 days after the foliar treatment had been applied. The tomatoes were fertilized a month before tissue samples were taken and again nine after the first fertilizer application (or about three weeks before the tissue samples were taken) with 12 grams per gallon of the 15-30-15. One gallon of fertilizer was poured over three replications of each set in the trial. Some of the plants had started to set fruit when the tissue samples were taken: R1T6-1 fruit (33.7 g), R2T6-1 fruit (9.8 g), R2T7-1 fruit (19.7 g), R2T2-1 fruit (6.3 g), R3T8-2 fruits (18.4, 3.4 g), R3T4-1 fruit (10.8 g), R3T1-1 fruit (26.5 g), R3T3-1 fruit (4 g).

| MICRO | CONTROL | TREATED | CHANGE | % |
|---|---|---|---|---|
| IDS COPPER | 5.9 | 51.7 | 45.8 | 783% |

| MICRO | CONTROL | TREATED | CHANGE | % |
|---|---|---|---|---|
| EDTA COPPER | 5.9 | 51.4 | 45.6 | 779% |
| IDS MANGANESE | 159.0 | 190.7 | 31.7 | 20% |
| EDTA MANGANESE | 159.0 | 173.3 | 14.3 | 9% |
| IDS ZINC | 35.0 | 106.8 | 71.8 | 205% |
| EDTA ZINC | 35.0 | 64.7 | 29.7 | 85% |

The results above shows the efficacy of the iminodisuccinate compounds of the present invention for providing necessary mineral nutrition to growing plants and seedlings. The trial shows the iminodisuccinate did as well as the EDTA for availability of the minerals.

EXAMPLE 15

In a preliminary lab synthesis trial, 61 grams of monoethanolamine were added to an Erlenmeyer flask submerged in an ice water bath. Then 49 grams of maleic anhydride were added to the flask with mechanical stirring. The mix was viscous and red in color. The reaction took place and the ethanolamine salt of N-ethanolmaleicamide was produced. The flask was hot to touch. While the blend was still warm, and while stirring, 54 grams of a 50% solution of potassium hydroxide were added to the blend. The blend was then allowed to deliquesce over night. Compounds of the present invention having the following formula resulted, where R is a hydroxyl, and n is 2:

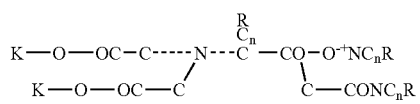

EXAMPLE 16

A five percent chelated iron solution was prepared by blending 18 ml of water with 100 grams of a (10% Fe) ferric nitrate solution. Once in solution, 82 grams of the compound produced in Example 10 was added. The finished solution was dark red, had a pH of 5, and was clear and free of precipitates. This chelated iron solution is suitable for blending with phosphorus fertilizers.

EXAMPLE 17

In a preliminary lab synthesis trial, 45 grams of monoethanolamine were added to an Erlenmeyer flask with 28 grams of potassium hydroxide. Then 49 grams of maleic anhydride were added to the flask with mechanical stirring. The reaction occurred producing heat; the mix was viscous and red in color. Once the blend cooled, 200 ml of water were added and a light orange-red solution of diethanolsuccinicamide-amino ethanol was produced, having the following formula, where X is potassium, R is a hydroxyl, and n is 2.

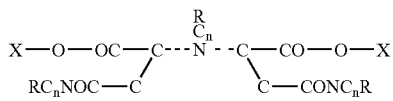

EXAMPLE 18

In 250 ml of water 1 gram of copper sulfate was added and mechanically stirred. To this solution, 10 ml of the diethanolsuccinamide-amino ethanol solution produced in Example 17 was added. The pH of the blend was adjusted to 8.4 and 1 gram of potassium phosphate was added the mixture. The blend was clear, dark blue and free of precipitates.

In another flask, 1 gram of copper sulfate was added to 250 ml of water and mechanically blended. Then, 1 gram of potassium phosphate was added to the blend. The pH of the solution was adjusted with potassium hydroxide. Immediately a powder solid was formed and precipitated. The hydroxide and phosphate salts of copper were formed. This example shows the utility of the compounds used as chelates.

EXAMPLE 19

In 25 ml of water, 20 ml of a 1.8M ferric nitrate was added. Once in solution, 30 ml of the diethanolsuccinamide amino ethanol solution produced in Example 17 was added and the pH of the blend was adjusted to 9.2. Then 1 gram of potassium phosphate was added to the mixture. The blend was clear, dark ruby red and free of precipitates.

In a separate flask, 25 ml of water, 20 grams of 1.8 M ferric nitrate and 1 gram of potassium phosphate were blended together and a light brown precipitate formed. When the pH was adjusted to 7 a very dark brown precipitate was formed.

Earlier work has shown the blends of phosphates with iminodisuccinate chelates are not stable solutions; in fact, on occasion insoluble hydroxides and insoluble phosphate salts would form at a neutral pH. This example shows the utility of the substituted Iminodisuccinates in phosphate solutions. Without the additional functionality added to the iminodisuccinate the compound fails to prevent the formation of insoluble hydroxide and phosphate salts in fertilizer solutions.

EXAMPLE 20

In 25 ml of water 1 gram of zinc sulfate was added. Once the zinc sulfate was in solution, 30 ml of the N,N-diethanolsuccinamide amino ethanol solution produced in Example 17 was added and the pH of the blend was adjusted to 9.5. Then 1 gram of potassium phosphate was added tho the mixture. The blend was clear, yellow, and free of precipitates.

In a separate flask 25 ml of water, 1 gram of zinc sulfate and 1 gram of potassium phosphate were blended together. Immediately a white precipitate formed.

Earlier work has shown that blends of phosphates with iminodisuccinate chelates are not stable solutions; in fact, insoluble hydroxides and insoluble phosphate salts would form at a neutral pH. This example shows the utility of the substituted Iminodisuccinates in phosphate solutions. Without the additional functionality added to the iminodisuccinate the compound fails to prevent the formation of insoluble hydroxide and phosphate salts in fertilizer solutions.

EXAMPLE 21

In 25 ml of water 10 ml of a manganese nitrate solution was added. Once the manganese nitrate was in solution, 30 ml of the N,N-diethanolsuccinamide amino ethanol solution produced in Example 17 was added to the mixture and the pH of the blend was adjusted to 6. Then 1 gram of potassium phosphate was added to the mixture. The blend was clear, amber in color, and free of precipitates.

Earlier work has shown the blends of phosphates with iminodisuccinate chelates are not stable solutions; in fact, insoluble hydroxides and insoluble phosphate salts would form at a neutral pH. This example shows the utility of the substituted Iminodisuccinates in phosphate solutions. Without the additional functionality added to the iminodisuccinate the compound fails to prevent the formation of insoluble hydroxide and phosphate salts in fertilizer solutions.

EXAMPLE 22

In a preliminary study, 2 grams of calcium chloride dihydrate were added to 200 ml of water and mechanically stirred. Then 20 ml of the diethanolsuccinamide amino ethanol solution produced in example 17 was added to the blend. The pH was adjusted to 9 producing a clear solution free of precipitates. When the pH of the solution is lowered to a pH of 5.5, phosphate salts can be added to the blend without calcium phosphate precipitate formation.

In another flask 2 grams of calcium chloride dihydrate were added to 200 ml of water and the pH was adjusted to 9. Almost immediately calcium hydroxide began to precipitate.

This example shows the utility of the substituted Iminodisuccinates in phosphate solutions. Without the additional functionality added to the iminodisuccinate the compound fails to prevent the formation of insoluble hydroxide and phosphate salts in fertilizer solutions.

EXAMPLE 23

Five drops of 1.8 M ferric nitrate were added to one liter of water and mechanically blended. Then 10 grams of potassium phosphate were added to the solution and allowed to form insoluble potassium salts. The potassium salt of succinic—2—aminoethanol, ethanolsuccinicamide, from Example 2 were added drop wise until the solution was clear, and then 10 ml of this clear solution of chelated minerals were added to 1000 ml of water and allowed to stand. No precipitates were formed.

Earlier work has shown that blends of phosphates with iminodisuccinate chelates are not stable solutions; in fact, insoluble hydroxides and insoluble phosphate salts would form at a neutral pH. This example shows the utility of the substituted Iminodisuccinates in phosphate solutions. Without the additional functionality added to the iminodisuccinate, the compound would fail to prevent the formation of insoluble hydroxide and phosphate salts in fertilizer solutions.

EXAMPLE 24

A five percent chelated manganese solution was prepared by blending 18 ml of water with 58 grams of a (17% Mn) manganese nitrate solution. Once the manganese nitrate was in solution, 82 grams of the compound produced in Example 10 was added. The finished solution was dark red, had a pH of 5, and was clear and free of precipitates. This chelated manganese solution is suitable for blending with phosphorus fertilizers.

EXAMPLE 25

In a preliminary lab synthesis trial, 45 grams of monoethanolamine were added to an Erlenmeyer flask with 28 grams of potassium hydroxide and 10 ml of water. The flask was then placed in an ice bath. Then 49 grams of maleic anhydride were added to the flask with mechanical stirring. A reaction occurred producing heat resulting in a compound that was viscous and orange-red in color. This compound has the following formula, where R is a hydroxyl and n is 4:

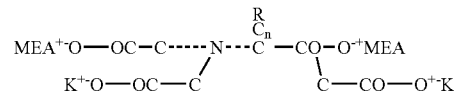

EXAMPLE 26

In 400 ml of water, 20 ml of a 10% ferric nitrate solution were added, and 20 ml of the product from example 25 were added. With mechanical stirring, 40 grams of monopotassium phosphate was added the mix. The pH of the solution was then adjusted to 2 with HCl. The pH of the solution was then gradually raised with the addition of base to a pH of 10. At a pH of 7 the solution changed color from yellow to red. At no point during the change of pH were any precipitates formed. This shows that the present compounds have a broad range of efficacy.

Earlier work taught that blends of phosphates with iminodisuccinate chelates are not stable solutions; in fact, insoluble hydroxides and insoluble phosphate salts would form at a pH greater then four.

This example shows the utility of the substituted Iminodisuccinates of the present invention in phosphate solutions. Without the additional functionality added to the iminodisuccinate the compound fails to prevent the formation of insoluble hydroxide and phosphate salts in fertilizer solutions.

EXAMPLE 27

In a preliminary lab synthesis trial, 61 grams of monoethanolamine were added to an Erlenmeyer flask and placed in an ice bath. Then 49 grams of maleic anhydride were added to the flask and ethanolmaleicamide was formed. Later, 112 grams of a 50% potassium hydroxide solution were added to the flask and stirred; Once the potassium hydroxide was in solution, 49 grams of maleic anhydride were then added to form a dipotassium salt of maleic acid. During the reaction, 58.62 grams of a 29.4% ammonium hydroxide solution was added. The reaction occurred producing heat; the mixture was viscous and bright red in color, and the blend was allowed to stir until cool. A blend of the following compounds was made:

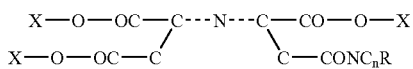

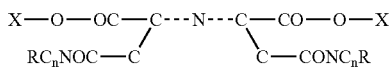

Where R is hydroxyl, n is 2, and X is potassium

EXAMPLE 28

In a preliminary lab synthesis trial, 50 grams of monoethanolamine were added to an Erlenmeyer flask with 28 grams of potassium hydroxide. The flask was then placed in an ice bath. Then 49 grams of maleic anhydride were then added to the flask with mechanical stirring. A reaction occurred producing heat; the mixture was viscous and bright red in color. It was allowed to stir until cool. The mixture or blend was then allowed to set overnight, after which 200 ml of water were blended in.

EXAMPLE 29

Synthesis of Poly Functional Poly Substituted Iminodisuccinic Acid

|  | Grams per mole | Grams needed for 1 mole | Grams needed for 0.25 Mol |
| --- | --- | --- | --- |
| MALEIC ANHYDRIDE | 98.06 | 196.12 | 49 |
| MONOETHANOL-AMINE | 61.0 | 122 | 62 |
| POTASSIUM HYDROXIDE | 56 | 168 | 42 |
| WATER | 18 | 48 | 16 |
| Total |  |  | 169 |

In a flask was placed 31 grams of monoethanolamine. Twenty-five grams of maleic anhydride were added, to produce a red liquid of ethanolmaleicamide. After the reaction, 16-ml of water and 31 grams of monoethanolamine were added to the flask. Once blended, 42 grams of potassium hydroxide were added and then immediately 25 additional grams of maleic anhydride were placed into the flask. Once the solution reacted, the mixture was allowed to cool. A clear yellow orange solution was produced.

EXAMPLE 30

In 400 ml of water, 20 ml of a 17% zinc nitrate solution were added and 60 ml of the product from example 28 were added. With mechanical stirring, 40 grams of monopotassium phosphate were added to the mix. The pH of the solution was then adjusted to 2 with HCl. The pH of the solution was then gradually raised with the addition of Monoethanolamine to a pH of 9. At no point during the change of pH were any precipitates formed, indicating the compounds have a broad range of efficacy.

Earlier work taught that blends of phosphates with iminodisuccinate chelates are not stable solutions; in fact, insoluble hydroxides and insoluble phosphate salts would form. This example shows the utility of the substituted Iminodisuccinates in phosphate solutions. Without the additional functionality added to the iminodisuccinate, the compound fails to prevent the formation of insoluble hydroxide and phosphate salts in fertilizers.

EXAMPLE 31

In 400 ml of water, 1 gram of copper sulfate was added and 10 ml of the product from example 28 were added. With mechanical stirring, 20 grams of monopotassium phosphate were added to the mix. The pH of the solution was then adjusted to 2 with HCl. The pH of the solution was then gradually raised with the addition of Monoethanolamine to a pH of 9. At no point during the change of pH were any precipitates formed, indicating that the present compounds have a broad range of efficacy.

Earlier work—prior art—taught that blends of phosphates with iminodisuccinate chelates were not stable solutions, in fact, insoluble hydroxides and insoluble phosphate salts would form at a neutral pH. This example shows the utility of the substituted Iminodisuccinates of this invention in phosphate solutions. Without the additional functionality added to the iminodisuccinate the compound fails to prevent the formation of insoluble hydroxide and phosphate salts in fertilizer solutions.

EXAMPLE 32

In 400 ml of water, 10 ml of 1.8 M ferric nitrate solution were added and 20 ml of the product from example 28 were added. With mechanical stirring, 20 grams of monopotassium phosphate was added to the mix. The pH of the solution was then adjusted to 2 with HCL. The pH of the solution was then gradually raised with the addition of Monoethanolamine to a pH of 10. At no point during the change of pH were any precipitates formed indicating that these compounds of this invention have a broad range of efficacy.

Earlier—prior art—work taught that blends of phosphates with iminodisuccinate chelates are not stable solutions' in fact, insoluble hydroxides and insoluble phosphate salts would form at a neutral pH. This example shows the utility of the substituted Iminodisuccinates of this invention in phosphate solutions. Without the additional functionality added to the iminodisuccinate the compound fails to prevent the formation of insoluble hydroxide and phosphate salts in fertilizer solutions.

EXAMPLES 33

One drop of 17% zinc nitrate, one drop of iron nitrate, and 0.1 gram of copper sulfate were added to one liter of water and mechanically blended. Then 10 grams of potassium phosphate were added to the solution and allowed to form insoluble potassium salts. The compounds from example 2 were added drop wise until the solution became clear. From this clear solution of chelated minerals 10 ml was then taken and added to 100 ml of water and allowed to stand. No precipitates were formed.

Earlier—prior art—work taught that blends of phosphates with iminodisuccinate chelates are not stable solutions, in fact, insoluble hydroxides and insoluble phosphate salts would form at a neutral pH. This example shows the utility of the substituted Iminodisuccinates of this invention in phosphate solutions. Without the additional functionality added to the iminodisuccinate the compound fails to prevent the formation of insoluble hydroxide and phosphate salts in fertilizer solutions.

EXAMPLE 34

A nine percent chelated zinc solution was prepared by blending 50 ml of water with 22.4 grams zinc oxide. Concentrated HCl was added until the solution was clear. Once in solution, 125 grams of the compound produced in Example 10 was added. The finished solution was red, had a pH of 5, and was clear and free of precipitates. This chelated zinc solution is suitable for blending with phosphorus fertilizers 2-ethanolaminesuccinic-N-ethanolsuccinicamide (tri potassium salt) has the following formula:

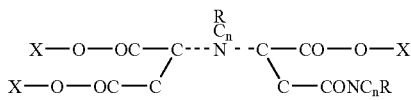

EXAMPLE 35

SYNTHESIS of N,N-DISUCCINICAMINOETHANOL (tetra potassium salt) 2 maleic anhydride(s)+4 KOH (aq)+1 monoethanolamine (1) _N,N-DISUCCINICAMINOETHANOL (tetra potassium salt)(s)

|  | Grams per mole | Grams needed for 1 mole of N,N—DISUCCINI CAMINOETHANOL (tetra potassium salt) | Grams needed for 0.25 Mol |
|---|---|---|---|
| MALEIC ANHYDRIDE | 98.06 | 196.12 | 49 |
| MONOETHANOLAMINE | 61.0 | 61 | 16 |
| POTASSIUM HYDROXIDE | 56 | 224 | 56 |
| WATER | 18 | 36 | 9 |
|  |  |  | 130 |

Potassium hydroxide was weighed out and added to the water. The monoethanolamine was then added to the blend and stirred in. Maleic anhydride was then added slowly and allowed to react to form N,N-disuccinic-amino-ethanol tetra potassium salt. The finished product was a light orange-red solid. The mixture was allowed to stand over night and 200 ml of water was then added to produce an orange-red clear 0.75 M solution of N,N-disuccinic-amino-ethanol tetra potassium salt, having the formula below, where R is a hydroxyl group and n is 2.

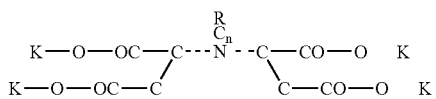

EXAMPLE 36

Yeild Quantification for N,N-Disuccinic-Amino-Ethanol (Tetra Potassium Salt)

To a beaker containing one liter of water, 20 grams of potassium phosphate were added to form a clear solution. To this solution, 10 grams of a 1.8 M ferric solution were added and ferric phosphate precipitated out of solution as a white solid. Later 2.4 grams of N,N-disuccinic-amino-ethanol tetra potassium salt, the solution produced in example 35, were added to this beaker still holding the ferric phosphate solids; and a clear yellow solution was produced inmediately.

For dilutions:

$(Concentration)_1 (volume\ in\ liters)_1 = (concentration)_2 (volume\ in\ liters)_2$ (1.8M ferric) (10 ml)=(1010 ml ferric/water dilution) (X)

X=0.018 M (2.4 ml of N,N-disuccinic-amino-ethanol tetra potassium salt) (0.75 M)=(1012.4 ml of the diluted chelated mix) (X)

X=0.018 M

The above example shows that the synthesis of the compound produced in example 35 yielded essentially 100% of the calculated product. Although isomerization is expected, and the nitrogen atom would still show chirality, the addition of the ethanol functionality allows for 100% of the calculated yield to be used as a high phosphate containing solution-chelating agent.

Earlier work has taught that blends of phosphates with iminodisuccinate chelates are not stable solutions; in fact, insoluble hydroxides and insoluble phosphate salts would form at a neutral pH. This example shows the utility of the substituted Iminodisuccinates of the present invention in phosphate solutions. Without the additional functionality added to the iminodisuccinate the compound fails to prevent the formation of insoluble hydroxide and phosphate salts in fertilizer solutions.

EXAMPLE 37

Ten ml of 17% zinc solution were added to a liter of water. Later 20 grams of potassium phosphate were added and dissolved. Zinc phosphate formed a precipitate. Phosphorous acid was then added to lower the pH and clear the solution. Once clear 30 ml of the solution prepared in example 35 was added. This acidic solution, which was acidic, then remained undisturbed for a day, after which the pH was adjusted to 10 with the addition of MEA. The zinc solution comprising chelated zinc remained clear, free of precipitates, and colorless.

Earlier work has taught that blends of phosphates with iminodisuccinate chelates are not stable solutions; in fact, insoluble hydroxides and insoluble phosphate salts would form at a neutral pH. In contrast, this example shows the utility of the substituted Iminodisuccinates of the present invention in phosphate solutions. Without the additional functionality added to the iminodisuccinate the compound fails to prevent the formation of insoluble hydroxide and phosphate salts in fertilizer solutions.

EXAMPLE 38

Two grams of basic copper sulfate were added to 200 ml of water. The pH of the solution was lowered to dissolve the copper. The solution prepared in example 29 was then added until the blend color changed from light blue to dark blue. The pH was then adjusted with MEA to 8. Five grams of potassium phosphate were next added to produce a clear, dark blue, solution.

Earlier work has taught that blends of phosphates with iminodisuccinate chelates are not stable solutions; in fact, insoluble hydroxides and insoluble phosphate salts would form. In contrast, this example shows the utility of the substituted Iminodisuccinates in phosphate solutions. Without the additional functionality added to the iminodisuccinate the compound fails to prevent the formation of insoluble hydroxide and phosphate salts in fertilizer solutions.

EXAMPLE 39

Thirty grams of 1.8 M ferric nitrate were added to 100 ml of water. The pH of the solution was lowered to 4 with phosphorous acid, and then 5 grams of Potassium phosphate were then added to the blend. Later 30 ml of the solution produced in example 29 was added. The pH was raised to 10 with KOH with out the formation of precipitates to produce a ruby red clear solution.

Earlier—prior art—work taught that the blends of phosphates with iminodisuccinate chelates are not stable solutions, in fact, insoluble hydroxides and insoluble phosphate salts would form. In contrast, this example shows the utility of the substituted Iminodisuccinates of the present invention in phosphate solutions. Without the additional functionality added to the iminodisuccinate the compound fails to prevent the formation of insoluble hydroxide and phosphate salts in fertilizer solutions.

EXAMPLE 40

In 500 ml of water, 1 gram of copper sulfate and 1 gram of potassium phosphate were added and stirred. The pH of the solution was raised to 8 and copper hydroxide and copper phosphate formed and precipitated. The blend was allowed to stand still until there were 2 distinct layers. The top layer was clear and colorless and the bottom layer was a light blue precipitate. The solution prepared in Example 28 was then added while mechanically stirring the mixture. The mixture turned dark blue and clear. This example shows the utility of the substituted Iminodisuccinates of the present invention in phosphate and hydroxide solutions.

EXAMPLE 41

SYNTHESIS of N,N-DISUCCINICAMINOETHANOL (tetra potassium salt)
2 maleic anhydride(s)+4 KOH (aq)+1 monoethanolamine (1)_N,N-DISUCCINICAMINOETHANOL (tetra potassium salt)(s)

|  | Grams per mole | Grams needed for 1 mole of N,N—DISUCCINI CAMINOETHANOL (tetra potassium salt) | Grams needed for 0.25 Mol |
| --- | --- | --- | --- |
| MALEIC ANHYDRIDE | 98.06 | 196.12 | 49 |
| MONOETHANOL-AMINE | 61.0 | 61 | 16 |
| POTASSIUM HYDROXIDE | 56 | 224 | 60 |
| WATER | 18 | 36 | 400 |

The monoethanolamine was added to the blend and stirred in. The maleic anhydride was then added slowly. Potassium hydroxide was weighed and added to the water and allowed to react to form the N,N-disuccinic-amino-ethanol tetra potassium salt. The finished product was light yellow solution, having the following formula, where R is a hydroxyl and n is 2.

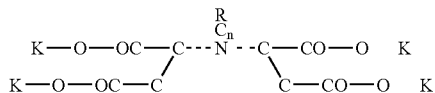

EXAMPLE 42

One hundred ml of the solution prepared in Example 41 was added to 500 ml of water and blended. 10 ml of 1.8-M ferric nitrate was then added to the mixture. Once a clear solution was formed at a pH of 10, ten grams of potassium phosphate were added to the solution to produce an orange-red clear solution without precipitates. The potassium salt of maleic acid was tested as a chelating agent.

In a separate flask 20 grams of maleic anhydride were blended in 500 ml of water. Potassium hydroxide was then added to the blend to raise the pH to 10. Later ten ml of 1.8M ferric nitrate was added to the mix and 10 grams of potassium phosphate was also blended in. When the mechanical blending stopped, a rust colored solid precipitated to form a layer at the bottom of the flask with a clear colorless layer above. The contents of the flask were then blended again while MEA was added to the mix. The precipitate never went back into solution. This work shows the compounds used for the synthesis of a substituted iminodisuccinate can not be used separately to achieve the results of the present invention.

The preferred compositions of the present invention may include one or more surfactants, which have been found to aid in preparation of other compositions and may assist in penetration of the active components upon application. Many types of surfactants may be used, including anionic, cationic, and amphoteric surfactants. Suitable nonionic surfactants for example without limitation include: polyoxy propylene polyoxyethylene block copolymers, alkyl aryl ethoxylates and or alkoxylates, fatty acid ethoxylates and or alkoxylates, fatty alcohol ethoxylates and or alkoxylates, fatty amine ethoxylates and or alkoxylates, vegetable or seed oil ethoxylates and or alkoxylates, sorbitan fatty acid ester ethoxylates and or alkoxylates, and alkyl polysaccharides.

The compositions of the present invention may be formulated in a wide range of forms known in the art. The compositions may, for example, be in the form of a concentrate to be diluted prior to application or it may be in the form of a granule, powder or liquid with a suitable solid or liquid carrier. For example, the compositions of this invention may be in the form of an emulsion, or dispersion in water, and, may comprise solvents or agricultural chemicals. Alternatively formulations of this invention may be adapted to form an emulsion when diluted with water prior to use.

Often those skilled in the art find synergistic combinations when blending or admixing plant growth regulating compounds. Frequently the active component is not acting synergistically but merely in combination with compounds known for producing a response.

Discussion of Possible Components for Admixes:

For their practical application, the compounds according to this invention are rarely used on their own. Instead they generally form part of formulations which also comprise a support and/or a surfactant in addition to active materials In the context of the invention, a support is an organic or mineral, natural or synthetic material with which the active material is associated to facilitate its application, for example, in the case of fertilizers, to the plant, to seeds or to soil, or to facilitate its transportation or handling. The support can be solid (e.g., clays, natural or synthetic silicates, resins, waxes, solid fertilizers) or fluid (e.g., water, alcohols, ketones, petroleum fractions, chlorinated hydrocarbons, liquefied gases, liquid fertilizers).

The surfactant can be an ionic or non-ionic emulsifier, dispersant or wetting agent such as, for example, salts of polyacrylic acids and lignin-sulphonic acids, condensates of ethylene oxide with fatty alcohols, fatty acids or fatty amines.

The compositions comprising the compounds of the present invention can be prepared in the form of wettable powders, soluble powders, dusting powders, granulates, solutions, emulsifiable concentrates, emulsions, suspended concentrates and aerosols.

The wettable powders according to the invention can be prepared in such a way that they contain the active material, and they often or typically contain, in addition to a solid support, a wetting agent, a dispersant and, when necessary, one or more stabilizers and/or other additives, such as, for example, penetration agents, adhesives or anti-lumping agents, colorants etc.

Aqueous dispersions and emulsions, such as, for example, compositions comprising the compounds of this invention obtained by diluting with water a wettable powder or an emulsifiable concentrate are also included within the general scope of the invention. These emulsions can be of the water-in-oil type or of the oil-in-water type, and can have a thick consistency resembling that of a "mayonnaise".

The compositions comprising the compounds of the present invention can contain other ingredients, for example protective colloids, adhesives or thickeners, thixotropic agents, stabilizers or sequestrants, as well as other active materials. A modest list of examples of possible formulation components for inclusion with the compositions of this invention follows without limitation.

Carbon Skeleton/Energy (CSE) Components:

The supposed function of this component is to supply carbon skeleton for synthesis of proteins and other molecules or to supply energy for metabolism. Water-soluble carbohydrates such as sucrose, fructose, glucose and other di- and monosaccharides are suitable, commonly in the form of molasses or other by-products of food manufacture. Commercially available lignosulfonates, discussed below under the heading "Complexing Agents," are also suitable as a CSE source inasmuch as they commonly contain sugars.

CSE Components:

Sugar—mannose, lactose, dextrose, erythrose, fructose, fucose, galactose, glucose, gulose, maltose, polysaccharide, raffinose, ribose, ribulose, rutinose, saccharose, stachyose, trehalose, xylose, xylulose, adonose, amylose, arabinose, fructose phosphate, fucose-p, galactose-p, glucose-p, lactose-p, maltose-p, mannose-p, ribose-p, ribulose-p, xylose-p, xylulose-p, deoxyribose, corn steep liquor, whey, corn sugar, corn syrup, maple syrup, grape sugar, grape syrup, beet sugar, sorghum molasses, cane molasses, calcium lignosulfonate sugar alcohol—adonitol, galactitol, glucitol, maltitol, mannitol, mannitol-p, ribitol, sorbitol, sorbitol-p, xylitol xxxx acids—glucuronic acid, a-ketoglutaric acid, galacturonic acid, glutaric acid, gluconic acid, pyruvic acid, poly galacturonic acid, saccharic acid, citric acid, succinic acid, malic acid, oxaloacetic acid, aspartic acid, phosphoglyceric acid, fulvic acid, ulmic acid, humic acid, glutamic acid.

Nucleotides and bases—adenosine, adenosine-p, adenosine-p-glucose, uridine, uridine-p, uridine-p-glucose, thymine, thymine-p, cytosine, cytosine-p, guanosine, guanosine-p, guanosine-p-glucose, guanine, guanine-p, NADPH, NADH, FMN, FADH The Macronutrient Components:

The macronutrients are essential to nutrition and growth. The most important macronutrients are N, P and K. Some example nitrogen compounds are: ammonium nitrate, monoammonium phosphate, ammonium phosphate sulfate, ammonium sulfate, ammonium phosphatenitrate, diammonium phosphate, ammoniated single superphosphate, ammoniated triple superphosphate, nitric phosphates, ammonium chloride, aqua ammonia, ammonia-ammonium nitrate solutions, calcium ammonium nitrate, calcium nitrate, calcium Cyanamid, sodium nitrate, urea, urea-formaldehyde, urea-ammonium nitrate solution, nitrate of soda potash, potassium nitrate, amino acids, proteins, nucleic acids.

Example Phosphate sources include: superphosphate (single, double and/or triple), phosphoric acid, ammonium phosphate, ammonium phosphate sulfate, ammonium phosphate nitrate, diammonium phosphate, ammoniated single superphosphate, ammoniated single superphosphate, ammoniated triple superphosphate, nitric phosphates, potassium pyrophosphates, sodium pyrophosphate, nucleic acid phosphates and phosphonic and phosphorous acid derivatives.

The potassium ion for example can be found in: potassium chloride, potassium sulfate, potassium gluconate, sulfate of potash magnesia, potassium carbonate, potassium acetate, potassium citrate, potassium hydroxide, potassium manganate, potassium phosphate, potassium molybdate, potassium thiosulfate, potassium zinc sulfate and the like.

Calcium sources include for example: calcium ammonium nitrate, calcium nitrate, calcium Cyanamid, calcium acetate, calcium acetylsalicylate, calcium borate, calcium borogluconate, calcium carbonate, calcium chloride, calcium citrate, calcium ferrous citrate, calcium glycerophosphate, calcium lactate, calcium oxide, calcium pantothenate, calcium propionate, calcium saccharate, calcium sulfate, calcium tartrate and the like.

Magnesium can be found for example in: magnesium oxide, dolomite, magnesium acetate, magnesium benzoate, magnesium bisulfate, magnesium borate, magnesium chloride, magnesium citrate, magnesium nitrate, magnesium phosphate, magnesium salicylate, magnesium sulfate.

Sulfur containing compounds include for example: ammonium sulfate, ammonium phosphate sulfate, calcium sulfate, potassium sulfate, magnesium sulfate, sulfuric acid, cobalt sulfate, copper sulfate, ferric sulfate, ferrous sulfate, sulfur, cysteine, methionine and elemental sulfur.

Micronutrient Components:

The most important micronutrients are or comprise: Zn, Fe, Cu, Mn, B, Co, and Mo.

Vitamin/Cofactor Components:

The most important are folic acid, biotin, pantothenic acid, nicotinic acid, riboflavin and thiamine and include for example: Thiamine—thiamine pyrophosphate, thiamine monophosphate, thiamine disulfide, thiamine mononitrate, thiamine phosphoric acid ester chloride, thiamine phosphoric acid ester phosphate salt, thiamine 1,5 salt, thiamine tri phosphoric acid ester, thiamine tri phosphoric acid salt, yeast, yeast extract Riboflavin—riboflavin acetyl phosphate, flavin adenine dinucleotide, flavin adenine mononucleotide, riboflavin phosphate, yeast, yeast extract. Nicotinic acid—nicotinic acid adenine dinucleotide, nicotinic acid amide, nicotinic acid benzyl ester, nicotinic acid monoethanolamine salt, yeast, yeast extract, nicotinic acid hydrazide, nicotinic acid hydroxamate, nicotinic acid-N-(hydroxymethyl)amide, nicotinic acid methyl ester, nicotinic acid mononucleotide, nicotinic acid nitrile. Pyridoxine—pyridoxal phosphate, yeast, yeast extract Folic acid—yeast, yeast extract, folinic acid. Biotin—biotin sulfoxide, yeast, yeast extract, biotin 4-amidobenzoic acid, biotin amidocaproate N-hydroxysuccinimide ester, biotin 6-amidoquinoline, biotin hydrazide, biotin methyl ester, d-biotin-N-hydroxysuccinimide ester, biotin-maleimide, d-biotin p-nitrophenyl ester, biotin propranolol, 5-(N-biotinyl)-3 aminoallyl)-uridine 5'-triphosphate, biotinylated uridine 5'-triphosphate, N-e-biotinyl-lysine. Pantothenic acid—yeast, yeast extract, coenzyme A, Cyanocobalamin—yeast, yeast extract. Phosphatidylcholine-soybean oil, eggs bovine heart, bovine brain, bovine liver, L-a-phosphatidylcholine, B-acetyl-g-O-alkyl, D-a-phosphatidylcholine(PTCn), B-acetyl-g-O-hexadecyl, DL-a-PTCh, B-acetyl-g-O-hexadecyl, L-a-PTCh, B-acetyl-g-O-(octadec-9-cis-enyl), L-a-PTCh, B-arachidonoyl, g-stearoyl, L-a-PTCh, diarachidoyl, L-a-PTCh, dibehenoyl (dibutyroyl, dicaproyl, dicapryloyl, didecanoyl, dielaidoyl, 12 diheptadecanoyl, diheptanoyl), DL-a-PTCh dilauroyl, L-a-PTCh dimyristoyl (dilauroyl, dilinoleoyl, dinonanoyl, dioleoyl, dipentadeconoyl, dipalmitoyl, distearoyl, diundecanoyl, divaleroyl, B-elaidoyl-a-palmitoyl, B-linoleoyl-a-palmitoyl) DL-a-PTCh di-O-hexadecyl (dioleoyl, dipalmitoyl, B-O-methyl-g-O-hexadecyl, B-oleoyl-g-O-hexadecyl, B-palmitoyl-g-O-hexadecyl), D-a-PTCh dipalmitoyl, L-a-PTCh, B-O-methyl-g-O-octadecyl, L-a-PTCh, B-(NBD-aminohex-anoyl)-g-palmitoyl, L-a-PTCh, B-oleoyl-g-O-palmitoyl (stearoyl), L-a-PTCh, B-palmitoyl-g-oleoyl, L-a-PTCh, B-palmitoyl-a-(pyren 1-yl) hexanoyl, L-a-PTCh, B(pyren-1-yl)-decanoyl-g-palmitoyl, L-a-PTCh, B-(pyren-1-yl)-hexanoyl-g-palmitoyl, L-a-PTCh, B-stearoyl-g-oleoyl. Inositol—inositol monophosphate, inositol macinate, myo-inositol, epi-inositol, myo-inositol 2,2'anhydro-2-c-hydroxymethyl (2-c-methylene-myo-inositol oxide), D-myo-inositol 1,4-bisphosphate, DL-myo-inositol 1,2-cyclic monophosphate, myo-inositol dehydrogenase, myo-inositol hexanicotinate, inositol hexaphosphate, myo-inositol hexasulfate, myo-inositol 2-monophosphate, D-myo-inositol 1-monophosphate, DL-myo-inositol 1-monophosphate, D-myo-inositol triphosphate, scyllo-inositol PABA—m-aminobenzoic acid, O-aminobenzoic acid, p-aminobenzoic acid butyl ester, PABA ethyl ester, 3-ABA ethyl ester.

Complexing Agents:

The function of this component, particularly in agricultural applications, aside from its proposed use as a Carbon skeleton agent, is to solubilize other components of the composition which otherwise may precipitate and become assailable or may immobilize minerals in the soil which might otherwise be unavailable to flora and fauna. Complexing agents such as, for example, citric acid, humic acids, lignosulfonate, etc. serve to tie up ions such as iron and prevent them from forming precipitates. In some cases this complexing is by way of chelation. These agents may form complexes with the following compounds for example: Citric acid; Ca, K, Na and ammonium lignosulfonates, fulvic acid, ulmic acid, humic acid, Katy-J, EDTA, EDDA (ethylenediaminedisuccinic acid), EDDHA, HEDTA, CDTA, PTPA, NTA, MEA, IDS, EDDS, and 4-phenylbutyric acid.

Other complexing agents include for example: Al and its salts, Zn—zinc oxide, zinc acetate, zinc benzoate, zinc chloride, zinc citrate, zinc nitrate, zinc salicylate, ziram Fe—ferric chloride, ferric citrate, ferric fructose, ferric glycerophosphate, ferric nitrate, ferric oxide (saccharated), ferrous chloride, ferrous citrate ferrous fumarate, ferrous gluconate, ferrous succinate. Mn—manganese acetate, manganese chloride, manganese nitrate, manganese phosphate, Cu—cupric acetate, cupric butyrate, cupric chlorate, cupric chloride, cupric citrate, cupric gluconate, cupric glycollate, cupric nitrate, cupric salicylate, cuprous acetate, cuprous chloride. B-calcium borate, potassium borohydride, borax, boron trioxide, potassium borotartrate, potassium tetraborate, sodium borate, sodium borohydride, sodium tetraborate and boric acid. Mo—molybdic acid, calcium molybdate, potassium molybdate, sodium molybdate. Co—cobaltic acetate, cobaltous acetate, cobaltous chloride, cobaltous oxalate, cobaltous potassium sulfate, cobaltous sulfate.

Growth Regulators:

Seaweed extract—kelp extract, Kinetin, Kinetin riboside, benzyladenine, zeatin riboside, zeatin, extract of corn cockle, isopentenyl adenine, dihydrozeatin, indoleacetic acid, phenylacetic acid, IBA, indole ethanol, indole acetaldehyde, indoleacetonitrile, indole derivitives, gibberellins (e.g. GA1, GA2, GA3, GA4, GA7, GA38 etc.) polyamines, monoethanolamine, allopurinol, GA inhibitors, ethylene inducing compounds, ethylene biosynthesis inhibitors, GABA, anticytokinins and antiauxins, ABA inducers and inhibitors, and other known growth regulators.

Gum Components:

Xanthan gum—guar gum, gum agar, gum accroides, gum arabic, gum carrageenan, gum damar, gum elemi, gum ghatti, gum guaiac, gum karya, locust bean gum, gum mastic, gum pontianak, gum rosin, gum storax, gum tragacanth Microbialstats, Proprionic Acid, Benzoic Acid, Sorbic Acid and Amino Acids.

Buffers

Phosphate buffer, formate or acetate buffer, AMP buffer, calcium tartrate, glycine buffer, phosphate citrate buffer, tris buffer, ECT.

If desired, a formulation or composition of the present invention may also include beneficial microorganisms. The compositions comprising the compounds of the present invention thus defined may be applied to plants by conventional methods including seed application techniques, as well as foliar methods.

The foregoing description of the invention has been directed in primary part to particular preferred embodiments in accordance with the requirements of the Patent Statutes and for purposes of explanation and illustration. It will be apparent, however, to those skilled in the art that many modifications and changes in the specifically described methods may be made without departing from the true scope and spirit of the invention. For example, while poly functional amide substituted iminodisuccinic acid or salt and a difunctional amine are preferred, other amide substituted iminodisuccinic acid or salt and amines may be used. In fact, soluble salts of the poly functional amide substituted iminodisuccinic salts may be used in place of the acids. Also, while it is preferred to dissolve the metal salt in an aqueous solution of the poly functional amide substitution on the iminodisuccinic acid to which the base is then added, the order of additive does not appear to be critical. Therefore, the invention is not restricted to the preferred embodiments described and illustrated but covers all modifications, which may fall within the scope of the following claims.

I claim:

1. A fertilizer for application to soil, seeds, or plants, comprising at least one metal selected from the group consisting of calcium, magnesium, manganese, iron, cobalt, copper, zinc, molybdenum, and mixtures thereof, chelated with a chelating composition comprising a modified iminodisuccinic acid, or a salt thereof, having one or more of the following formulas:

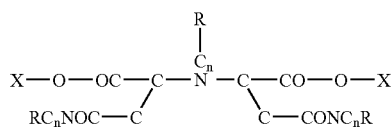
(a)

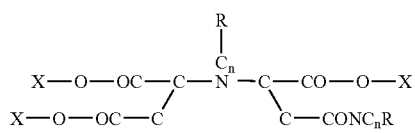
(b)

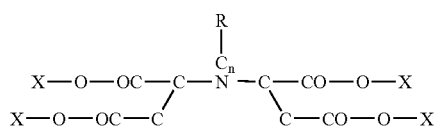
(c)

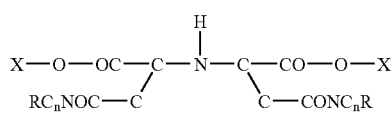
(d)

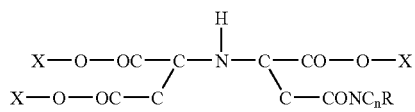
(e)

where X may be H, alkali, alkaline earth, ammonium-substituted radical, ammonium or transition metal;
where n may be 1 to 10; and
where R may be a Lewis base capable of donating a nonbonded pair of electrons, prepared such that said chelating composition has at least six coordinating nonbonded electrons; and at least five of the nonbonded electron pairs may participate in coordination without steric hindrance or bond angle limitations.

2. A fertilizer for application to soils, seeds or plants comprising: water; at least one metal salt selected from the group consisting of the alkaline earth and transition metals, and inorganic Lewis bases or inorganic or organic amines or combinations, wherein the inorganic Lewis bases or inorganic or organic amines or combinations are selected from the group of polyfunctional amines consisting of organic alkylamines, allylamines, arylamines, diamines, hydroxylamines, polyamines, polyhydroxyamines, acid amines, and mixtures or derivatives thereof; and a chelating composition comprising a modified iminodisuccinic acid, or a salt thereof, having one or more of the following formulas:

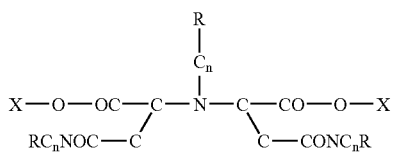
(a)

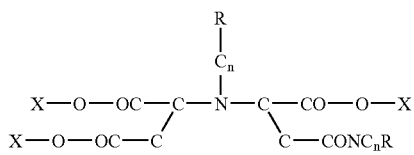
(b)

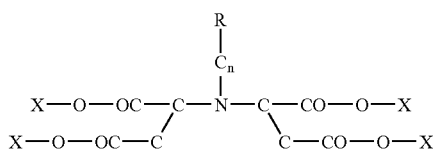
(c)

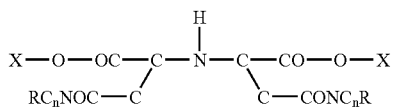
(d)

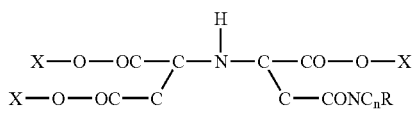
(e)

where X may be H, alkali, alkaline earth, ammonium-substituted radical, ammonium or transition metal;
where n may be 1 to 10; and
where R may be a Lewis base capable of donating a nonbonded pair of electrons, prepared such that said chelating composition has at least six coordinating nonbonded electrons; and at least five of the nonbonded electron pairs may participate in coordination without steric hindrance or bond angle limitations.

3. A fertilizer additive for application to soil, seeds, or plants, comprising a chelating composition having at least one poly functional substitution on iminodisuccinic acid having the following formula:

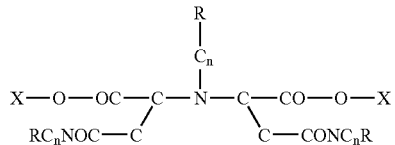

where X is H, alkali, alkaline earth, ammonium-substituted radical, ammonium or transition metal; n is 1 to 10, and R is a Lewis base capable of donating a nonbonded pair of electrons, wherein said compound is synthesized in a single reaction vessel at ambient pressure without the addition of heat, by a synthesis comprising the steps of:
  (a) adding an acid anhydride or lactone to a first polyfunctional amine, and allowing same to react to form a N-polyfunctional acid common name amide; and
  (b) adding water, alkali metal hydroxide, and a second polyfunctional amine to said N-polyfunctional acid common name amide and allowing same to react to form an imino di N-polyfunctional acid common name amide, such that said compound has at least six coordinating nonbonded electrons; and at least five of the nonbonded electron pairs may participate in coordination without steric hindrance or bond angle limitations.

4. A fertilizer for application to soil, seeds, or plants, comprising water, at least one nutrient selected from the group consisting of nitrogen, phosphorus and potassium, and a chelating agent in a concentration of $1/10^a$ to 1 part, where a is less then 10, or $1.0 \times 10^{-9}$ Molar to 3 Molar, wherein said chelating agent comprises at least one poly functional substitution on iminodisuccinic acid having the following formula:

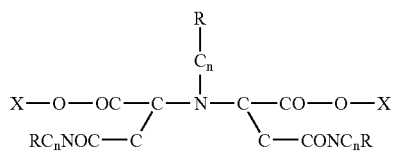

where X is H, alkali, alkaline earth, ammonium-substituted radical, ammonium or transition metal; n is 1 to 10, and R is a Lewis base capable of donating a nonbonded pair of electrons, and wherein said chelating agent is synthesized in a single reaction vessel at ambient pressure without the addition of heat, by a synthesis comprising the steps of:
  (a) adding an acid anhydride or lactone to a first polyfunctional amine, and allowing same to react to form a N-polyfunctional acid common name amide; and
  (b) adding water, Alkali metal hydroxide, and a second polyfunctional amine to said N-polyfunctional acid common name amide and allowing same to react to form an imino di N-polyfunctional acid common name amide, such that said chelating agent has at least six coordinating nonbonded electrons; and at least five of the nonbonded electron pairs may participate in coordination without steric hindrance or bond angle limitations.

5. A fertilizer for application to soils, seed, or plants, wherein said fertilizer comprises a chelating compound comprising at least one poly functional substitution on iminodisuccinic acid having the following formula:

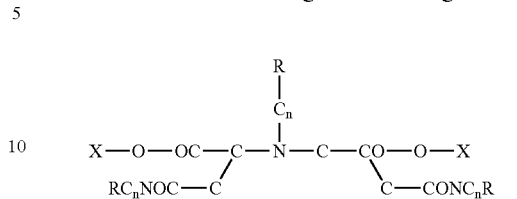

where X is H, alkali, alkaline earth, ammonium-substituted radical, ammonium or transition metal; n is 1 to 10, and R is a Lewis base capable of donating a nonbonded pair of electrons, and wherein said compound is synthesized by a synthesis comprising the steps of:
  (a) adding an acid anhydride or lactone to a first polyfunctional amine, and allowing same to react to form a N-polyfunctional acid common name amide; and
  (b) adding water, alkali metal hydroxide, and a second polyfunctional amine to said N-polyfunctional acid common name amide and allowing same to react to form an imino di N-polyfunctional acid common name amide, such that said chelating compound has at least six coordinating nonbonded electrons; and at least five of the nonbonded electron pairs may participate in coordination without steric hindrance or bond angle limitations.

6. A fertilizer comprising a compound having at least one poly functional substitution on iminodisuccinic acid having the following formula:

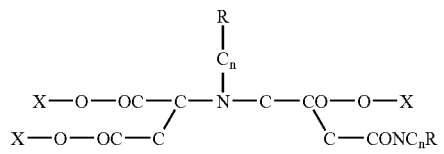

where X is H, alkali, alkaline earth, ammonium-substituted radical, ammonium or transition metal salts, n is 1 to 10, R is a Lewis base capable of donating a nonbonded pair of electrons, and wherein the synthesis of said compound is in a single reaction vessel at ambient pressure without the addition of heat, and comprises the steps of:
  (a) adding an acid anhydride or lactone to a first polyfunctional amine, and allowing same to react to form a N-polyfunctional acid common name amide; and
  (b) adding to said N-polyfunctional acid common name amide, water, a second polyfunctional amine, an acid anhydride or lactone, an alkali metal hydroxide, and allowing same to react to form said mpound, such that said compound has at least six coordinating nonbonded electrons; and at least five of the nonbonded electron pairs may participate in coordination without steric hindrance or bond angle limitations.

7. A fertilizer comprising a chelating agent in a concentration of $1/10^a$ to 1 part, where a is less then 10, or $1.0 \times 10^{-9}$ Molar to 3 Molar, said chelating agent comprising at least one poly functional substitution on iminodisuccinic acid having the following formula:

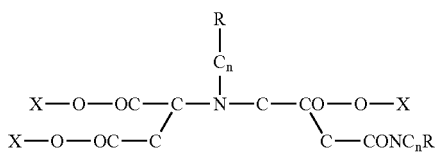

where X is H, alkali, alkaline earth, ammonium-substituted radical, ammonium or transition metal salts, n is 1 to 10, R is a Lewis base capable of donating a nonbonded pair of electrons, wherein the synthesis of said chelating agent comprises the steps of:
(a) adding an acid anhydride or lactone to a first polyfunctional amine, and allowing same to react to form a N-polyfunctional acid common name amide; and
(b) adding to said N-polyfunctional acid common name amide, water, a second polyfunctional amine, an acid anhydride or lactone, an alkali metal hydroxide, and allowing same to react to form said chelating agent in a single reaction vessel at ambient pressure without the addition of heat.

8. A compound used for application to soils, seed, or plants, in fertilizer, said compound comprising at least one poly functional substitution on iminodisuccinic acid having the following formula:

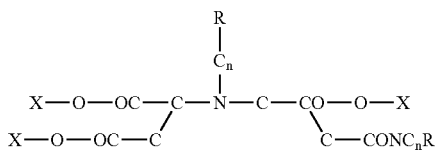

where X is H, alkali, alkaline earth, ammonium-substituted radical, ammonium or transition metal salts, n is 1 to 10, R is a Lewis base capable of donating a nonbonded pair of electrons, and Me is selected from the alkali metals, wherein the synthesis of said compound comprises the steps of:
(a) adding an acid anhydride or lactone to a first polyfunctional amine, and allowing same to react to form a N-polyfunctional acid common name amide; and
(b) adding to said N-polyfunctional acid common name amide, water, a second polyfunctional amine, an acid anhydride or lactone, a Me (OH), and allowing same to react to form said compound,
such that said compound has at least six coordinating nonbonded electrons; and at least five of the nonbonded electron pairs may participate in coordination of a mineral for fertilizer without steric hindrance or bond angle limitations.

9. A fertilizer additive comprising at least one poly functional substitution on iminodisuccinic acid having the following formula:

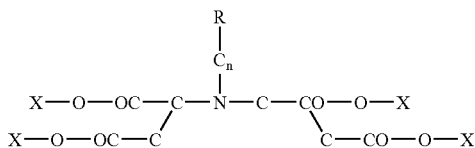

where X is H, alkali, alkaline earth, ammonium-substituted radical, ammonium or transition metal salts; where n is 1 to 10; where R is a Lewis base capable of donating a non-bonded pair of electrons, wherein the synthesis of said fertilizer additive comprises the steps of:
adding maleic anhydride or malic acid to Me (OH)+polyfunctional amine+water, and allowing same to react to form the N,N-disuccinicamino(:functional group) such that said additive has at least six coordinating nonbonded electrons; and at least five of the nonbonded electron pairs may participate in coordination of a mineral for fertilizer without steric hindrance or bond angle limitations.

10. A chelating agent in a concentration of $1/10^a$ to 1 part, where a is less than 10, or, or $1.0 \times 10^{-9}$ Molar to 3 Molar, wherein said chelating agent comprises at least one poly functional substitution on iminodisuccinic acid having the following formula:

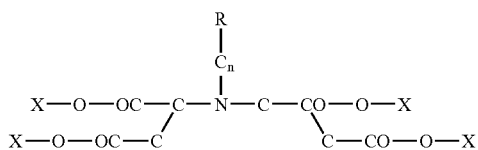

where X is H, alkali, alkaline earth, ammonium-substituted radical, ammonium or transition metal salts; where n is 1 to 10; where R is a Lewis base capable of donating a non-bonded pair of electrons, and wherein the synthesis of said chelating agent comprises the steps of: adding maleic anhydride or malic acid to Me (OH)+polyfunctional amine+water, and allowing same to react to form the N,N-disuccinicamino(:functional group),
prepared such that said chelating agent has at least six coordinating nonbonded electrons; and at least five of the nonbonded electron pairs may participate in coordination of a mineral for fertilizer without steric hindrance or bond angle limitations, enabling the chelating agent to be useful in fertilizer.

11. A fertilizer compound used for application to soils, seed, or plants comprising at least one poly functional substitution on iminodisuccinic acid having the following formula:

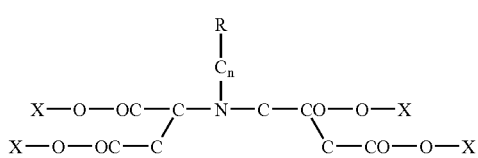

where X is H, alkali, alkaline earth, ammonium-substituted radical, ammonium or transition metal salts; where n is 1 to 10; where R is a Lewis base capable of donating a non-bonded pair of electrons, wherein the synthesis of said compound comprises the steps of: adding maleic anhydride or malic acid to Me (OH)+polyfunctional amine+water, and allowing same to react to form the N,N-disuccinicamino(:functional group);
wherein said compound has at least six coordinating non-bonded electrons; and at least five of the nonbonded electron pairs may participate in coordination of a mineral for fertilizer without steric hindrance or bond angle limitations.

12. A fertilizer additive comprising at least one poly functional substitution on iminodisuccinic acid having the following formula:

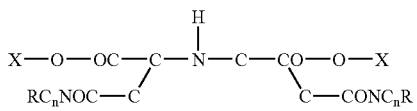

where X is H, alkali, alkaline earth, ammonium-substituted radical, ammonium or transition metal salts; where n is 1 to 10, where R is a Lewis base capable of donating a nonbonded pair of electrons; wherein the synthesis of said fertilizer additive comprises the steps of:
  (a) adding acid anhydride or lactone to a first polyfunctional amine and allowing same to react to form a N-polyfunctional acid common name amide; and
  (b) adding to said N-polyfunctional acid common name amide, water+ammonia+Alkali metal hydroxide, and allowing same to react to form an N,N-amino polyfunctional acid common name amide, such that said additive has at least six coordinating nonbonded electrons; and at least five of the nonbonded electron pairs may participate in coordination of a mineral for fertilizer without steric hindrance or bond angle limitations.

13. A chelating agent in a concentration of $\frac{1}{6^a}$ to 1 part, where a is less then 10, or $1.0 \times 10^{-9}$ Molar to 3 Molar, said chelating agent comprising at least one poly functional substitution on iminodisuccinic acid having the following formula:

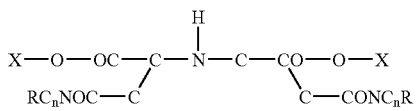

where X is H, alkali, alkaline earth, ammonium-substituted radical, ammonium or transition metal salts; where n is 1 to 10, where R is a Lewis base capable of donating a nonbonded pair of electrons; and wherein the synthesis of said chelating agent comprises the steps of:
  (a) adding acid anhydride or lactone to a first polyfunctional amine and allowing same to react to form a N-polyfunctional acid common name amide; and
  (b) adding to said N-polyfunctional acid common name amide, water+ammonia+Alkali metal hydroxide, and allowing same to react to form an N,N-amino polyfunctional acid common name amide, such that said chelating agent has at least six coordinating nonbonded electrons; and at least five of the nonbonded electron pairs may participate in coordination of a mineral without steric hindrance or bond angle limitations.

14. A compound used for application to soils, seed, or plants comprising at least one poly functional substitution on iminodisuccinic acid having the following formula:

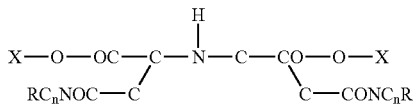

where X is H, alkali, alkaline earth, ammonium-substituted radical, ammonium or where X is H, alkali, alkaline earth, ammonium-substituted radical, ammonium or transition metal salts; where n is 1 to 10, where R is a Lewis base capable of donating a nonbonded pair of electrons; and wherein the synthesis of said compound comprises the steps of: (a) adding acid anhydride or lactone to a first polyfunctional amine and allowing same to react to form a N-polyfunctional acid common name amide; and (b) adding to said N-polyfunctional acid common name amide, water+ammonia+Me(OH), and allowing same to react to form an N,N-amino polyfunctional acid common name amide, such that said compound has at least six coordinating nonbonded electrons; and at least five of the nonbonded electron pairs may participate in coordination of a mineral without steric hindrance or bond angle limitations.

15. A fertilizer additive comprising at least one poly functional substitution on iminodisuccinic acid having the following formula:

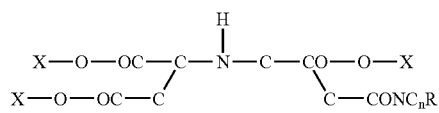

where X may be H, alkali, alkaline earth, ammonium-substituted radical, ammonium or transition metal; where n may be 1 to 10; where R may be a Lewis base capable of donating a nonbonded pair of electrons; wherein the synthesis of said fertilizer additive comprises the steps of:
  (a) adding an acid anhydride or lactone to a first polyfunctional amine and allowing same to react to form an N-polyfunctional acid common name amide;
  (b) adding to said N-polyfunctional acid common name amide, water, ammonia+maleic anhydride or maleic acid (salt) and allowing same to react to form said fertilizer additive, such that said additive has at least six coordinating nonbonded electrons; and at least five of the nonbonded electron pairs may participate in coordination of a mineral for fertilizer without steric hindrance or bond angle limitations.

16. A chelating agent in a concentration of $\frac{1}{6^a}$ to 1 part, where a is less then 10, or $1.0 \times 10^{-9}$ Molar to 3 Molar, said chelating agent comprising at least one poly functional substitution on iminodisuccinic acid having the following formula:

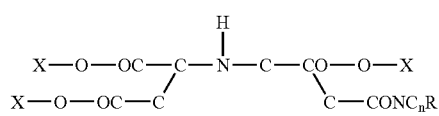

where X may be H, alkali, alkaline earth, ammonium-substituted radical, ammonium or transition metal; where n may be 1 to 10; where R may be a Lewis base capable of donating a nonbonded pair of electrons; wherein the synthesis of said chelating agent comprises the steps of:
  (a) adding an acid anhydride or lactone to a first polyfunctional amine and allowing same to react to form an N-polyfunctional acid common name amide;
  (b) adding to said N-polyfunctional acid common name amide, water, ammonia+maleic anhydride or maleic acid (salt) and allowing same to react to form said chelating agent, prepared such that said chelating agent has at least six coordinating nonbonded electrons; and at least five of the nonbonded electron pairs may participate in coordination of a mineral without steric hindrance or bond angle limitations.

17. A compound used for application to soils, seed, or plants, said compound comprising at least one poly functional substitution on iminodisuccinic acid having the following formula:

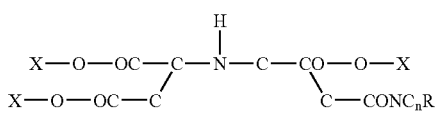

where X may be H, alkali, alkaline earth, ammonium-substituted radical, ammonium or transition metal; where n may be 1 to 10; where R may be a Lewis base capable of donating a nonbonded pair of electrons; wherein the synthesis of said compound comprises the steps of:
   (a) adding an acid anhydride or lactone to a first polyfunctional amine and allowing same to react to form an N-polyfunctional acid common name amide;
   (b) adding to said N— polyfunctional acid common name amide, water, ammonia+maleic anhydride or maleic acid (salt) and allowing same to react to form said compounds prepared such that said compound has at least six coordinating nonbonded electrons; and at least five of the nonbonded electron pairs may participate in coordination of a mineral without steric hindrance or bond angle limitations.

18. A fertilizer additive comprising iminodisuccinic acid having the following formula:

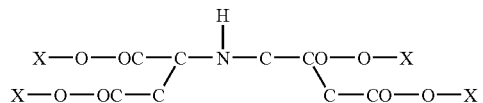

where X is H, alkali, alkaline earth, ammonium-substituted radical, ammonium or transition metal salt, prepared such that said additive has at least six coordinating nonbonded electrons; and at least five of the nonbonded electron pairs may participate in coordination of a mineral for fertilizer without steric hindrance or bond angle limitations.

19. An iminodisuccinic acid used for application to soils, seed, or plants having the following formula:

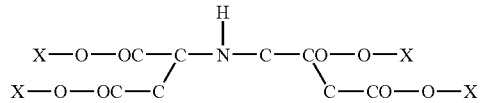

where X is H, alkali, alkaline earth, ammonium-substituted radical, ammonium or transition metal salt, prepared such that said acid has at least six coordinating nonbonded electrons; and at least five of the nonbonded electron pairs may participate in coordination of a mineral for fertilizer without steric hindrance or bond angle limitations.

* * * * *